United States Patent
Shin et al.

(10) Patent No.: US 10,704,193 B2
(45) Date of Patent: Jul. 7, 2020

(54) REDUCTION DYEING FOR INDIGO USING BACTERIAL STRAIN

(71) Applicant: INDUSTRY FOUNDATION OF CHONNAM NATIONAL UNIVERSITY, Buk-gu, Gwangju (KR)

(72) Inventors: Youn Sook Shin, Gwangju (KR); Geun-Joong Kim, Gwangju (KR); Eun Sil Choi, Gwangju (KR); Kyung Hee Son, Gwangju (KR)

(73) Assignee: INDUSTRY FOUNDATION OF CHONNAM NATIONAL UNIVERSITY, Gwangju (KR)

(*) Notice: Subject to any disclaimer, the term of this patent is extended or adjusted under 35 U.S.C. 154(b) by 144 days.

(21) Appl. No.: 15/971,580

(22) Filed: May 4, 2018

(65) Prior Publication Data

US 2018/0251938 A1 Sep. 6, 2018

Related U.S. Application Data

(62) Division of application No. 14/906,170, filed as application No. PCT/KR2014/000356 on Jan. 13, 2014, now abandoned.

(30) Foreign Application Priority Data

Jul. 19, 2013 (KR) .................. 10-2013-0085315

(51) Int. Cl.
*D06P 1/22* (2006.01)
*C12R 1/01* (2006.01)
*C12N 1/20* (2006.01)
*D06P 1/00* (2006.01)

(52) U.S. Cl.
CPC .............. *D06P 1/228* (2013.01); *C12N 1/20* (2013.01); *C12R 1/01* (2013.01); *D06P 1/0004* (2013.01); *D06P 1/221* (2013.01)

(58) Field of Classification Search
CPC ........ D06P 1/228; D06P 1/0004; D06P 1/221; C12R 1/01
See application file for complete search history.

(56) References Cited

FOREIGN PATENT DOCUMENTS

| JP | 2007-110913 A | 5/2007 |
|---|---|---|
| KR | 10-1104820 B1 | 1/2012 |
| KR | 10-2012-0092244 A | 8/2012 |
| KR | 10-1225448 B1 | 1/2013 |
| KR | 10-1249252 B1 | 4/2013 |

OTHER PUBLICATIONS

Mojca Bozic, et al., "Enzymatic reduction of complex redox dyes using NADH-dependent reductase from Bacillus subtilis coupled with cofactor regeneration", Appl Microbiol Biotechnol, 2010, pp. 563-571, vol. 85.
Mojca Bozic, et al., "Voltametric monitoring of enzyme-mediated indigo reduction in the presence of various fibre materials", Enzyme and Microbial Technology, 2009, pp. 317-323, vol. 45.
Kenichi Aino, et al., "Bacterial community characterization and dynamics of indigo fermentation", Federation of European Microbiological Societies, 2010, pp. 174-183, vol. 74.
International Searching Authority, International Search Report for PCT/KR2014/000356 dated Apr. 9, 2014 [PCT/ISA/210].
International Searching Authority, Written Opinion for PCT/KR2014/000356 dated Apr. 9, 2014 [PCT/ISA/237].
Khodaiyan et al., Effect of Culture Conditions on Canthaxanthin Production by Dietzia natronolimnaea HS-1, J. Microbiol. Biotechnol., 2007, vol. 17, No. 2, pp. 195-201.
Collins et al., *Nesterenkonia lacusekhoensis* sp. nov., isolate! from hyper saline Ekho Lake, East Antarctica, and emended description of the genus *Nesterenkonia*, International Journal of Systematic Evolutionary Microbiology (2002), 52, 1145-1150.
Compendium of Actinobacteria from Dr. Joachim m. Wink, University of Braunschweig, International Journal of Systematic Evolutionary Microbiology (2002), 52, 1145-1150.
Staley et al., Prosthecomicrobium and Ancalomicrobium: New Prosthecate Freshwater Bacteria, Journal of Bacteriology, May 1968, pp. 921-1942.

*Primary Examiner* — Kade Ariani
(74) *Attorney, Agent, or Firm* — Sughrue Mion, PLLC

(57) ABSTRACT

Provided is a reduction dyeing method for indigo color using *Nesterenkonia* sp. KDB2, KDB3 and/or KDB4. The reduction dyeing method is relatively simple, efficient and allows good reproducibility, by using *Nesterenkonia* sp. KDB2, KDB3 and/or KDB4 bacterial strains instead of a traditional fermentation process which entails poor reproducibility and is exacting and complicated.

7 Claims, 20 Drawing Sheets
Specification includes a Sequence Listing.

1. *Dietzia natronolimnaea* strain TPL19    *Dietzia* sp. KDB1         KC433534
2. *Nesterenkonia* sp. AC84                 *Nesterenkonia* sp. KDB2   KC433535
3. *Dietzia natronolimnaea* strain W5044    *Nesterenkonia* sp. KDB3   KC433536
4. *Nesterenkonia* sp. 110-8                *Nesterenkonia* sp. KDB4   KC433537

| Strain amount (mg) | Sample |
|---|---|
| 7 |  |
| 20 |  |
| 40 |  |
| 60 |  |

| Strain amount (mg) | Sample |
|---|---|
| 20 |  |
| 40 |  |
| 60 |  |

| Strain amount (mg) | Sample |
|---|---|
| 7 |  |
| 20 |  |
| 40 |  |
| 60 |  |

| Strain amount (mg) | Sample |
|---|---|
| 20 |  |
| 40 |  |
| 60 |  |
| 100 |  |

| Strain amount (mg) | Sample |
|---|---|
| 7 |  |
| 20 |  |
| 40 |  |
| 60 |  |

| Strain amount (mg) | Sample |
|---|---|
| 20 |  |
| 60 |  |
| 100 |  |

| Strain amount (mg) | Sample |
|---|---|
| 7 |  |
| 20 |  |
| 40 |  |
| 60 |  |

| Strain amount (mg) | Sample |
|---|---|
| 20 |  |
| 40 |  |
| 60 |  |
| 100 |  |

| Strain amount (mg) | Sample |
|---|---|
| 40 |  |
| 60 |  |
| 100 |  |

SEQUENCE LISTING

<160> NUMBER OF SEQ ID NOS: 6

<210> SEQ ID NO 1
<211> LENGTH: 1463
<212> TYPE: DNA
<213> ORGANISM: Unknown
<220> FEATURE:
<223> OTHER INFORMATION: Indigo dyeing bacteria

<400> SEQUENCE: 1

```
agggtttttt aactggctca ggacgaacgc tggcggcgtg cttaacacat gcaagtcgaa    60
cggtaaggcc ctttcggggg tacacgagtg gcgaacgggt gagtaacacg tgggtaatct   120
gccctgcact tcgggataag cctgggaaac cgggtctaat accggatatg agctcctgcc   180
gcatggtggg ggttggaaag tttttcggtg caggatgagt ccgcggccta tcagcttgtt   240
ggtggggtaa tggcctacca aggcgacgac gggtagccgg cctgagaggg tgatcggcca   300
cactgggact gagacacggc ccagactcct acgggaggca gcagtgggga atattgcaca   360
atgggcgaaa gcctgatgca gcgacgccgc gtggggatg acggtcttcg gattgtaaac   420
tcctttcagt agggacgaag cgaaagtgac ggtacctgca gaagaagcac cggccaacta   480
cgtgccagca gccgcggtaa tacgtagggt gcaagcgttg tccggaatta ctgggcgtaa   540
agagctcgta ggcggtttgt cacgtcgtct gtgaaatcct ccagctcaac tgggggcgtg   600
caggcgatac gggcagactt gagtactaca ggggagactg gaattcctgg tgtagcggtg   660
aaatgcgcag atatcaggag gaacaccggt ggcgaaggcg ggtctctggg tagtaactga   720
cgctgaggag cgaaagcatg gggagcaaac aggattagat accctggtag tccatgccgt   780
aaacggtggg cgctaggtgt ggggtccttc cacggattcc gtgccgtagc taacgcatta   840
agcgccccgc ctggggagta cggccgcaag gctaaaactc aaaggaattg acggggccc   900
gcacaagcgg cggagcatgt ggattaattc gatgcaacgc gaagaacctt acctaggctt   960
gacatataca ggacgacggc agagatgtcg tttcccttgt ggcttgtata caggtggtgc  1020
atggttgtcg tcagctcgtg tcgtgagatg ttgggttaag tcccgcaacg agcgcaaccc  1080
ctgtctcatg ttgccagcac gttatggtgg ggactcgtga gagactgccg gggtcaactc  1140
ggaggaaggt ggggatgacg tcaaatcatc atgcccctta tgtctagggc ttcacacatg  1200
ctacaatggc tagtacagag ggctgcgaga ccgcgaggtg gagcgaatcc cttaaagcta  1260
gtctcagttc ggattggggt ctgcaactcg acccatgaa gtcggagtcg ctagtaatcg  1320
cagatcagca ttgctgcggt gaatacgttc ccgggccttg tacacaccgc ccgtcacgtc  1380
atgaaagtcg gtaacacccg aagccggtgg cctaacccct gtgggaggga gccgtcgaaa  1440
```

```
gtgggatcgg cattggacac aca                                           1463
```

<210> SEQ ID NO 2
<211> LENGTH: 1518
<212> TYPE: DNA
<213> ORGANISM: Nesterenkonia sp.
<220> FEATURE:
<223> OTHER INFORMATION: Nesterenkonia sp. KDB 2

<400> SEQUENCE: 2

```
agggtttgtt tttcgctcag gatgaacgct ggcggcgtgc ttaacacatg caagtcgaac     60
gatgaagacc gtgcttgcac ggttggatta gtggcgaacg ggtgagtatc acgtgagtaa    120
ccttcccttg actctgggat aagcccggga aactgggtct aataccggat acgaccagtc    180
ctcgcatggg gtgctggtgg aaagatttat cggtcttgga tggactcgcg gcctatcagc    240
ttgttggtga ggtaatggct caccaaggcg atgacgggta gccggcctga gagggtgacc    300
ggccacactg ggactgagac acggcccaga ctcctacggg aggcagcagt ggggaatatt    360
gcacaatggg cgaaagcctg atgcagcgac gccgcgtgcg ggatgacggc cttcgggttg    420
taaaccgctt tcagcaggga agaagcgaaa gtgacggtac ctgcagaaga agcgccggct    480
aactacgtgc cagcagccgc ggtaatacgt agggcgcgag cgttatccgg aattattggg    540
cgtaaagagc tcgtaggcgg tttgtcacgt ctgctgtgaa agcccgaggc tcaacctcgg    600
gtgtgcagtg ggtacgggca gactagagtg cagtagggga gactggaatt cctggtgtag    660
cggtgaaatg cgcagatatc aggaggaaca ccgatggcga aggcaggtct ctgggctgtt    720
actgacgctg aggagcgaaa gcatggggag cgaacaggat tagataccct ggtagtccat    780
gccgtaaacg ttgggcacta ggtgtggggg acattccacg ttttccgcgc cgtagctaac    840
gcattaagtg ccccgcctgg ggagtacggc cgcaaggcta aaactcaaag gaattgacgg    900
gggcccgcac aagcggcgga gcatgcggat taattcgatg caacgcgaag aaccttacca    960
aggcttgaca tggaccggat cgctgcagag atgcagtttc ccttcggggt cggttcacag   1020
gtggtgcatg gttgtcgtca gctcgtgtcg tgagatgttg ggttaagtcc cgcaacgagc   1080
gcaaccccta tcctatgttg ccagcacgtg atggtgggga ctcatgggag actgccgggg   1140
tcaactcgga ggaaggtggg gacgacgtca atcatcatg ccccttatgt cttgggcttc   1200
acgcatgcta caatggccgg tacaatgggt tgcgatactg tgaggtggag ctaatcccta   1260
aaagccggtc tcagttcgga tcgaagtctg caactcgact tcgtgaagtt ggagtcgcta   1320
gtaatcgcag atcagcaacg ctgcggtgaa tacgttcccg ggccttgtac acaccgcccg   1380
tcaagtcacg aaagtgggta cacccgaagc cggtggcct aaccccttgtg gggggagccg   1440
tcgaaagtgg gactcgcgat tggatatata aaaggaggg ggatatatat atatataaat   1500
aagagcgccc cgtctttta                                                1518
```

<210> SEQ ID NO 3
<211> LENGTH: 1530
<212> TYPE: DNA
<213> ORGANISM: Nesterenkonia sp.
<220> FEATURE:
<223> OTHER INFORMATION: Nesterenkonia sp. KDB 3

<400> SEQUENCE: 3

```
aaggtttcca ggaaactgct caggatgaac gctggcggcg tgcttaacac atgcaagtcg     60
aacgatgaag accgtgcttg cacggttgga ttagtggcga acgggtgagt atcacgtgag    120
taaccttccc ttgactctgg gataagcccg ggaaactggg tctaataccg gatacgacca    180
```

```
gtcctcgcat ggggtgctgg tggaaagatt tatcggtctt ggatggactc gcggcctatc    240
agcttgttgg tgaggtaatg gctcaccaag gcgatgacgg gtagccggcc tgagagggtg    300
accggccaca ctgggactga gacacggccc agactcctac gggaggcagc agtggggaat    360
attgcacaat gggcgaaagc ctgatgcagc gacgccgcgt gcgggatgac ggccttcggg    420
ttgtaaaccg ctttcagcag gaagaagcg aaagtgacgg tacctgcaga agaagcgccg    480
gctaactacg tgccagcagc cgcggtaata cgtaggcgc gagcgttatc cggaattatt    540
gggcgtaaag agctcgtagg cggtttgtca cgtctgctgt gaaagcccga ggctcaacct    600
cgggtgtgca gtgggtacgg gcagactaga gtgcagtagg ggagactgga attcctggtg    660
tagcggtgaa atgcgcagat atcaggagga acaccgatgg cgaaggcagg tctctgggct    720
gttactgacg ctgaggagcg aaagcatggg gagcgaacag gattagatac cctggtagtc    780
catgccgtaa acgttgggca ctaggtgtgg gggacattcc acgttttccg cgccgtagct    840
aacgcattaa gtgccccgcc tggggagtac ggccgcaagg ctaaaactca aaggaattga    900
cgggggcccg cacaagcggc ggagcatgcg gattaattcg atgcaacgcg aagaaccttA    960
ccaaggcttg acatggaccg gatcgctgca gagatgcagt ttcccttcgg ggtcggttca   1020
caggtggtgc atggttgtcg tcagctcgtg tcgtgagatg ttgggttaag tcccgcaacg   1080
agcgcaaccc ctatcctatg ttgccagcac gtaatggtgg ggactcatgg gagactgccg   1140
gggtcaactc ggaggaaggt ggggacgacg tcaaatcatc atgccccttA tgtcttgggc   1200
ttcacgcatg ctacaatggc cggtacaatg ggttgcgata ctgtgaggtg gagctaatcc   1260
ctaaaagccg gtctcagttc ggatcgaagt ctgcaactcg acttcgtgaa gttggagtcg   1320
ctagtaatcg cagatcagca acgctgcggt gaatacgttc ccgggccttg tacacaccgc   1380
ccgtcaagtc acgaaagtgg gtaacacccg aagccggtgg cctaacccttA gtgggggag   1440 ccgtcgaaag tgggactcgc gattggatat acaaggggg gggcgcatat atatataa    1500 aagggggggg cggctctctt cttgtggagg                                    1530
```

<210> SEQ ID NO 4
<211> LENGTH: 1518
<212> TYPE: DNA
<213> ORGANISM: Nesterenkonia sp.
<220> FEATURE:
<223> OTHER INFORMATION: Nesterenkonia sp. KDB 4

<400> SEQUENCE: 4

```
aggtttgatt ctcgctcagg atgaacgctg gcggcgtgct taacacatgc aagtcgaacg     60
atgaagaccg tgcttgcacg gttggattag tggcgaacgg gtgagtatca cgtgagtaac    120
cttcccttga ctctgggata agcccggaa actgggtcta ataccggata cgaccagtcc    180
tcgcatgggg tgctggtgga aagatttatc ggtcttggat ggactcgcgg cctatcagct    240
tgttggtgag gtaatggctc accaaggcga tgacggtag ccggcctgag agggtgaccg    300
gccacactgg gactgagaca cggcccagac tcctacggga gcagcagtg ggaatattg     360 cacaatgggc gaaagcctga tgcagcgacg ccgcgtgcgg gatgacggcc ttcgggttgt    420
aaaccgcttt cagcagggaa gaagcgaaag tgacggtacc tgcagaagaa gcgccggcta    480
actacgtgcc agcagccgcg gtaatacgta gggcgcgagc gttatccgga attattgggc    540
gtaaagagct cgtaggcggt ttgtcacgtc tgctgtgaaa gcccgaggct caacctcggg    600
tgtgcagtgg gtacgggcag actagagtgc agtagggag actggaattc ctggtgtagc    660
```

```
ggtgaaatgc gcagatatca ggaggaacac cgatggcgaa ggcaggtctc tgggctgtta    720
ctgacgctga ggagcgaaag catggggagc gaacaggatt agatacctg gtagtccatg     780 ccgtaaacgt tgggcactag gtgtggggga cattccacgt tttccgcgcc gtagctaacg    840
cattaagtgc cccgcctggg gagtacggcc gcaaggctaa aactcaaagg aattgacggg    900
ggcccgcaca agcggcggag catgcggatt aattcgatgc aacgcgaaga accttaccaa    960
ggcttgacat ggaccggatc gctgcagaga tgcagtttcc cttcggggtc ggttcacagg   1020
tggtgcatgg ttgtcgtcag ctcgtgtcgt gagatgttgg gttaagtccc gcaacgagcg   1080
caacccctat cctatgttgc cagcacgtga tggtggggac tcatgggaga ctgccggggt   1140
caactcggag aaggtgggg acgacgtcaa atcatcatgc cccttatgtc ttgggcttca    1200
cgcatgctac aatggccggt acaatggggt gcgatactgt gaggtggagc taatccctaa   1260
aagccggtct cagttcggat cgaagtctgc aactcgactt cgtgaagttg gagtcgctag   1320
taatcgcaga tcagcaacgc tgcggtgaat acgttcccgg gccttgtaca caccgcccgt   1380
caagtcacga aagtgggtaa cacccgaagc cgtggccta  accttgtgg ggggagccgt    1440 cgaaagtggg actcgcgttg gatatacaaa gagggggggg cggagatata tatataaaaa   1500
agggagagag gtgtagta                                                 1518

<210> SEQ ID NO 5
<211> LENGTH: 20
<212> TYPE: DNA
<213> ORGANISM: artifical sequence
<220> FEATURE:
<223> OTHER INFORMATION: primer 27F

<400> SEQUENCE: 5
agagtttgat cmtggctcag                                                 20

<210> SEQ ID NO 6
<211> LENGTH: 19
<212> TYPE: DNA
<213> ORGANISM: artifical sequence
<220> FEATURE:
<223> OTHER INFORMATION: primer 1492R

<400> SEQUENCE: 6
ggttaccttg ttacgactt                                                  19
```

REDUCTION DYEING FOR INDIGO USING BACTERIAL STRAIN

CROSS REFERENCE TO RELATED APPLICATIONS

This Application is a Divisional Application of U.S. application Ser. No. 14/906,170, filed Mar. 23, 2016, which is a National Stage of International Application No. PCT/KR2014/000356 filed Jan. 13, 2014, claiming priority based on Korean Patent Application No. 10-2013-0085315 filed Jul. 19, 2013, the contents of all of which are incorporated herein by reference in their entirety.

TECHNICAL FIELD

The present invention relates to reduction dyeing for natural indigo and synthetic indigo using a bacterial strain, and an eco-friendly reduction dyeing method for indigo having more excellent efficiency and reproducibility by using bacteria isolated and identified from a fermentation dyeing liquid of traditional indigo dyes, and a bacterial strain used for the same.

BACKGROUND ART

Indigo is not dissolved in water. When the indigo is reduced under alkaline conditions, the indigo is changed into a leuco compound which is soluble to have affinity for various fibers. The water-soluble structure is oxidized and changed into an insoluble structure, such that color is exhibited. In Korea, fermentation dyeing using fresh juice salt and niram has been mainly performed, and the fermentation dyeing requires a reduction (fermentation) process at the time of requiring the niram, and a method of adding carbohydrate components such as corn syrup, etc., based on lye in connection with the reduction is known. However, the reduction fermentation conditions are strict and complicated, such that a precise technology depending on a lot of time, labor, and experience, is required.

In addition, a method for reducing insoluble indigo to water-soluble leuco-indigo may be mainly divided into a chemical reduction method using sodium hydrosulfite ($Na_2S_2O_4$) which is a commercially and commonly available and strong reducing agent and a biological reduction method using microorganisms, such as a traditional manner of dyeing method (Bozic et al. 2009, Enzyme and Microbial Technology 45(4):317-323). However, the biological reduction method using microorganisms is a time-consuming process and is difficult to apply in actual industries since specific microbial species or amounts are not defined. Therefore, the chemical reduction process using the strong reducing agent such as sodium hydrosulfite or sodium sulfide ($Na_2S$) is used in actual industrial applications (Bozic et al. 2010, Applied Microbiology and Biotechnology 85(3):563-571).

However, the chemical reduction using the reducing agent such as sodium hypochlorite or sodium sulfide causes a number of environmental problems and coloring instability, and has strong reducing power, such that when the reducing agent is discharged to an external environment, it may seriously harm an aerobic environment, and thus, various problems may occur in waste water treatment (Aino et al., 2010, FEMS Microbiology Ecology 174(1):174-183).

Above all, the reduction process is difficult to be standardized, which is the biggest obstacle to modernizing traditional indigo dyeing.

DISCLOSURE

Technical Problem

An object of the present invention is to provide a method for reducing indigo that identifies physiological properties of a microorganism by separating the microorganism capable of reducing indigo without using a chemical reducing agent having a harmful effect on the environment, and uses the properties, and a microorganism used for the same.

Further, another object of the present invention is to provide an eco-friendly indigo reduction method applicable to synthetic indigo as well as to natural indigo, having high reproducibility, simplified, and having a good dye uptake, while overcoming disadvantages in that at the time of indigo dyeing using bacteria involved in natural fermentation, a long time is required depending on an external environment, success or failure is uncertain, and color reproducibility is not sufficient.

Technical Solution

In one general aspect, there is provided four kinds of novel microorganisms each having an indigo reduction ability.

That is, the present invention provides a *Dietzia* sp. KDB1 having an indigo reduction ability.

The present invention provides a *Nesterenkonia* sp. KDB2 having an indigo reduction ability.

The present invention provides a *Nesterenkonia* sp. KDB3 having an indigo reduction ability.

The present invention provides a *Nesterenkonia* sp. KDB4 having an indigo reduction ability.

In another general aspect, there is provided a microbial agent for indigo reduction including any one strain of the *Dietzia* sp. KDB1, the *Nesterenkonia* sp. KDB2, the *Nesterenkonia* sp. KDB3, and the *Nesterenkonia* sp. KDB4 strains or a mixed strain thereof, as an effective ingredient.

In still another general aspect, there is provided a production method of a microbial agent for indigo reduction including any one strain of the *Dietzia* sp. KDB1, the *Nesterenkonia* sp. KDB2, the *Nesterenkonia* sp. KDB3, and the *Nesterenkonia* sp. KDB4 strains or a mixed strain thereof, as an effective ingredient.

In still another general aspect, there is provided a reduction dyeing method for indigo using any one strain of the *Dietzia* sp. KDB1, the *Nesterenkonia* sp. KDB2, the *Nesterenkonia* sp. KDB3, and the *Nesterenkonia* sp. KDB4 strains or a mixed strain thereof.

The reduction dyeing method for indigo according to the present invention may be performed in an alkaline aqueous solution.

The *Dietzia* sp. KDB1, the *Nesterenkonia* sp. KDB2, the *Nesterenkonia* sp. KDB3, and the *Nesterenkonia* sp. KDB4 strains according to the present invention may be gram-positive bacteria having an activity to nitrogen source assimilation.

Advantageous Effects

The reduction dyeing for indigo using a bacterial strain according to the present invention is simple and eco-friendly, and effectively reduces both of natural indigo and synthetic indigo to effectively increase dye uptake of fabric.

In addition, in the reduction dyeing for indigo using the bacterial strain, the reduction rate of the indigo may be increased to improve economic efficiency for coloring utilization.

BEST MODE

Figure 1:
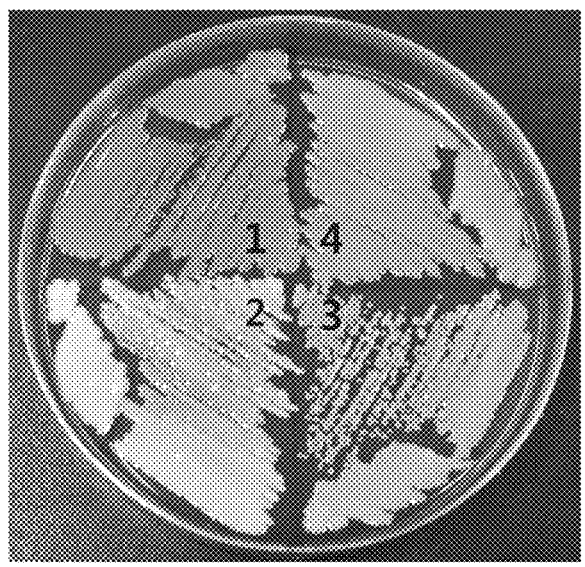
FIG. 1 shows four kinds of strains separated from a traditional fermentation vat.

The present invention provides bacterial strains having indigo reduction ability and a reduction dyeing method for indigo using the bacterial strains In addition, the present invention provides a microbial agent including the bacterial strains having the indigo reduction ability or mixed strains thereof, as an effective ingredient, and a production method thereof.

The present invention provides an eco-friendly reduction dyeing method for indigo capable of effectively increasing dye uptake of fabric by effectively reducing both of natural indigo and synthetic indigo through simple process.

In addition, in the reduction dyeing for indigo using the bacterial strain, the reduction rate of the indigo may be increased to improve economic efficiency for coloring utilization.

Hereinafter, although the present invention is described in more detail through the following exemplary embodiments, the present invention is not limited to Examples defining the gist. Meanwhile, it is obvious to a person skilled in the art that the present invention is not limited to process conditions provided by the Examples below, and may be randomly selected within the scope of the conditions required for achieving objects of the present invention.

The present invention provides bacterial strains having indigo reduction ability.

More specifically, the bacterial strain having the indigo reduction ability according to the present invention may be any one of *Dietzia* sp. KDB1, *Nesterenkonia* sp. KDB2, *Nesterenkonia* sp. KDB3, and the *Nesterenkonia* sp. KDB4 strains.

The accession number of the *Dietzia* sp. KDB1 was requested at Genebank Center, Korean Agricultural Culture Collection) on May 23, 2013, and given on Jun. 26, 2013 (Accession No. KACC91821P).

The accession of the *Dietzia* sp. KDB1 was approved at Korean Collection for Type Cultures, Korea Research Institute Bioscience and Biotechnology (KRIBB) on Dec. 4, 2013 (Accession No. KCTC 12524BP).

The accession number of the *Nesterenkonia* sp. KDB2 was requested at Genebank Center, Korean Agricultural Culture Collection on May 23, 2013, and given on Jun. 26, 2013 (Accession No. KACC91822P).

In addition, the accession of the *Nesterenkonia* sp. KDB2 was approved at Korean Collection for Type Cultures, Korea Research Institute Bioscience and Biotechnology (KRIBB) on Dec. 4, 2013 (Accession No. KCTC 12525BP).

The accession number of the *Nesterenkonia* sp. KDB3 was requested at Genebank Center, Korean Agricultural Culture Collection on May 23, 2013, and given on Jun. 26, 2013 (Accession No. KACC91823P).

In addition, the accession of the *Nesterenkonia* sp. KDB3 was approved at Korean Collection for Type Cultures, Korea Research Institute Bioscience and Biotechnology (KRIBB) on Dec. 4, 2013 (Accession No. KCTC 12526BP).

The accession number of the *Nesterenkonia* sp. KDB4 was requested at Genebank Center, Korean Agricultural Culture Collection on May 23, 2013, and given on Jun. 26, 2013 (Accession No. KACC91824P).

In addition, the accession of the *Nesterenkonia* sp. KDB4 was approved at Korean Collection for Type Cultures, Korea Research Institute Bioscience and Biotechnology (KRIBB) on Dec. 4, 2013 (Accession No. KCTC 12527BP).

Further, the present invention provides a microbial agent for indigo reduction including: the strain or culture fluid thereof, as an effective ingredient.

The microbial agent for indigo reduction of the present invention may be produced by using the *Dietzia* sp. KDB1, the *Nesterenkonia* sp. KDB2, the *Nesterenkonia* sp. KDB3, and the *Nesterenkonia* sp. KDB4 alone as an effective ingredient or by mixing these strains.

As non-limited examples, the microbial agent for indigo reduction of the present invention may be produced by using the *Dietzia* sp. KDB1 alone as an effective ingredient, or by mixing the *Dietzia* sp. KDB1 and the *Nesterenkonia* sp.

KDB2, or by mixing all of four kinds thereof, but the present invention is not limited thereto.

When the microbial agent for indigo reduction is produced by mixing four kinds of strains according to the present invention, a reducing effect for indigo may be improved.

The microbial agent for indigo reduction of the present invention may be produced into solvents, powders, suspensions, dispersions, emulsions, oil dispersions, pastes, dusts, diffusion material or granules, but the present invention is not limited thereto. Further, the microbial agent for indigo reduction may be used by spraying, atomizing, dusting, scattering or pouring. The usage forms depend on intended purposes, and in all cases, distribution of the microbial agent according to the present invention needs to be fine and uniform as much as possible.

Hereinafter, a process and a method for screening microorganisms each having an indigo reduction ability are described through the Examples of the present invention.

Material and Method

1) DNA extraction for Bacterial Community Analysis from traditional fermentation broth DNAs were extracted from a dyeing solution with good dyeing ability made in 2008 and 2010 and a dyeing solution with poor dyeing ability made in 2009, respectively, among dyeing solutions made by traditional fermentation method in Naju, Jeollanam-do Province. The fermentation broths used in the experiments were stored at −70° C. before extracting the DNAs. Each fermentation broth was subjected to centrifugation at 13000 rpm for 10 minutes, and the obtained precipitate (0.1 g to 0.2 g) was suspended in sterile distilled water (5 ml). From the obtained product (1 ml), genomic DNA was extracted by Genomic DNA Purification Kit (Promega).

2) Construction and Screening of 16s rRNA Library 16s rRNA library was constructed by using forward 27F (5'-AGAGTTTGATCMTGGCTCAG-3')(SEQ ID NO: 5), reverse 1492R (5'-GGTTACCTTGTTACGACTT-3')(SEQ ID NO: 6) universal primers. PCR was performed using Taq polymerase for amplification of genes, wherein condition for the PCR included denaturation at 95° C. for 10 minutes, extension at 95° C., and denaturation for 1 minute, annealing at 58° C. for 1 minute, and extension at 72° C. for 1.5 minute, and the number of cycles was 25 cycles. The amplified PCR product was developed by electrophoresis on agarose gel for 30 minutes. The corresponding band to 1.5 to 1.6 kb was cut on the gel and purified by a PCR Clean-Up kit (Qiagen, Inc.). The purified 16s rRNA DNA was ligated by using a pGEM vector system (Promega) and a T-Blunt vector system (Solgent), and transformed into E. coli XL1-Blue. Then, for screening, the transformant was cultured in a Macconkey solid medium including ampicillin (50 μg/ml), and white colonies were screened.

3) Confirmation of Microbial Community Through Restriction Fragment Length Polymorphism (RFLP)

From the screened clones, whether or not 16s rRNA is inserted was confirmed by colony cracking, and cultured in an LB ampicillin (50 μg/ml) liquid medium. Then, plasmids were extracted by using a miniprep DNA purification system kit (Qiagen, Inc.) from the strains induced by the culturing. The amplified 16s rRNAs were treated with a cocktail enzyme solution including BamHII EcoRI, and HindIII having six recognition sequences among restriction enzymes recognizing and cutting specific sequence portion of the gene. This test was to analyze and classify patterns of fragment shown on the gel, and recognize four specific sequences to treat Sau3AI having high cutting frequency, and re-analyzing the fragment shown on the gel, wherein clones having different patterns were final-screened to analyze base sequence. For pattern analysis, the extracted DNA (12-25 ng) was used and mixed with a cocktail enzyme solution (BamHII, EcoRI, HindIII) and Sau3AI enzyme 0.5-1U, respectively, followed by reaction for 1 hour and 30 minutes to 3 hours. Then, electrophoresis was performed on 1.2% agarose gel for 30 minutes, and 8% polyacrylamide gel for 2 hours and 30 minutes, respectively, at 100V, and the patterns cut by the restriction enzyme were compared. The plasmid DNA with different patterns was subjected to PCR by forward (27F, 5'-AGAGTTTGATCCTGGCTCAG-3') (SEQ ID NO: 5) and reverse (1492R, 5'-GGTTACCTTGT-TACGACTT-3')(SEQ ID NO: 6) primers, and Taq polymerase for amplifying 16s rRNA. Condition for the PCR included denaturation at 95° C. for 10 minutes, denaturation at 95° C. for 1 minute, annealing at 58° C. for 1 minute, and extension at 72° C. for 1.5 minute, and the number of cycles was 25 cycles. The amplified PCR product was developed by electrophoresis on agarose gel for 30 minutes, and a portion of band (1.5 to 1.6 kb) was cut on the gel and purified by a PCR Clean-Up kit (Promega). The sequence analysis of the purified 16s rDNA was requested at Genotech and Macrogen for sequence confirmation. In Genotech, the sequences were read from both ends of 16s rDNA by using forward (27F) and reverse (1492R) primers. In Macrogen, the sequence analysis was performed in the manner of reading sequences from the middle of 16s rDNA by using the forward (518F) and reverse (800R) primers. From the obtained two results, the final sequences were confirmed by using sequence alignment program (DNAMAN®, CLU-WTALW). The confirmed sequences were compared with 16s rDNA sequences of the strain registered in GeneBank Database using Blast program provided by NCBI, and the strain confirmed from the fermentation broth was identified and the system was confirmed.

TABLE 1

<Composition of reaction solution for amplifying 16s rRNA gene>

| Component | μl |
| --- | --- |
| Colony | — |
| 27F Primer (5 pmol) | 0.5 |
| 1492R Primer (5 pmol) | 0.5 |
| dNTFs (10 mM) | 1 |
| 10X PCR Buffer | 2.5 |
| DDW | 20.2 |
| Taq Polymerase | 0.3 |
| Final Volume | 25 |

TABLE 2

<Condition of reaction solution for amplifying 16s rRNA gene>

| | Reaction Temperature | Reaction Time | Reaction Cycle |
| --- | --- | --- | --- |
| Initial Denaturation | 94° C. | 5 Minutes | 1 Cycle |
| Denaturation | 94° C. | 1 Minute | 25 Cycles |
| Annealing | 58° C. | 1 Minute | — |
| Polymerization | 72° C. | 1.5 Minutes | — |

4) Screening of Culturable Strains from Traditional Fermentation Broth

In order to culture strains capable of being separated among complex microflora in the fermentation dyeing solution, nutrient medium (1% tryptone, 0.5% yeast extract, 0.3 g beef extract, 5% NaCl and pH 10) was modified based on the strain identification result using 16s rRNA sequence, and used. The fermentation broth was plated on a nutrient medium according to dilution magnification, and cultured at 30° C. for 4 days. In addition, in order to find strains grown in the minimal medium using indican as a sole carbon source, the fermentation broth was cultured under the same condition as in the M9 minimal nutrient medium using indican (indoxyl-glucose) which is a precursor of indigo dye as a carbon source. Among the cultured stains, the target bacterial strains were screened depending on general phenotypic differences, and whether or not the indican is used as a carbon source.

5) Strain Identification using Gram-staining

Through 16s rRNA gene sequence comparison, it was confirmed that the most similar strain was a gram-positive bacterium. In order to clearly confirm this, determination for gram-positive bacterium was performed through gram-staining. Sterilized distilled water was dropped onto a slide-glass and the bacterium was applied thereonto. The slide-glass was dried by indirect heat so that the bacterium was fixed. A crystal violet staining reagent was added on the slide-glass tilted so as to flow into the dried bacterium, starting from the edge of the slide-glass, followed by reaction for 1 minute. The staining reagent was washed by flowing distilled water at the back of the slide-glass. An iodine solution was added and reacted for 1 minute. The reacted product was washed by the same method as described above, and 95% ethanol was allowed to flow for decolorization. The product was washed with distilled water, and a safranin staining reagent was added and reacted for 1 minute. The product was washed with distilled water, and moisture was removed. Then, whether staining is performed was confirmed by a microscope.

6) Strain identification using KOH Test

The gram staining method is the most basic method for classifying and identifying bacteria. However, there are some cases that gram-positive bacteria are stained as a gram-negative bacterium, such that there is often false-negative result. In particular, in anaerobic bacteria, there is a more frequent possibility in which the gram-positive bacteria are discolored as compared to other bacteria, and there is a case in which the gram-positive bacteria are discolored even by culture condition. Meanwhile, *Mobiluncus* sp. strain has the same structure as a cell wall of gram-positive bacteria, such both (positive and negative) of gram stain results are shown. The KOH test firstly described in 1938 by Ryu is a method using a difference in the cell membrane components between positive bacteria and negative bacteria. That is, the cell membrane of the gram-positive bacteria is relatively stable in a low concentration of KOH solution, but the cell membrane of the gram-negative bacteria is easily destroyed, and DNA is released, and the released DNA increases viscosity to generate a string phenomenon. 20 µl of 3% KOH solution (3% KOH in 10% glycerin solution stored at room temperature) (20 µl) was dropped onto a glass plate, and two to three colonies were mixed. Gram-positive and gram-negative are capable of being determined by observing a phenomenon that viscosity is increased for 30 to 60 seconds. A case in which viscosity was strongly shown within 0 to 60 seconds was determined as gram-positive, and a case in which viscosity was strongly shown after 60 seconds was determined as gram-negative. In general, in the gram-negative bacteria, it could be confirmed that viscosity was increased within 15 seconds, and in the gram-positive bacteria, longer time was needed, and viscosity was not shown.

7) Strain Identification by Analysis of Biochemical Properties

For strain identification, physiological properties, biochemical properties, shapes, and cultural properties were confirmed. Genus may be confirmed by the shapes and the cultural properties, but confirmation of species requires to identify physiological properties and biochemical properties. For strain identification, a test was conducted to confirm biochemical properties of each strain.

① This test was to measure protein hydrolysis activity. The protein hydrolysis activity could be confirmed by adding mercury chloride ($HgCl_2$) to a transparent ring formed by the strains grown in skim milk agar medium were formed. Skim milk (0.5%) was added to a nutrient plate medium including yeast extract 3 g/1 L, peptone 8 g/1 L, and agar 10 g/1 L, and the strains were cultured in the medium Hydrolytic activity for casein was confirmed by adding 10% mercury chloride ($HgCl_2$)/20% hydrochloric acid (HCl) solution to the transparent ring formed by growing the strains.

② In order to confirm the decomposition ability for starch, a test medium was produced by adding 0.15% soluble starch to a nutrient plate medium (yeast extract 3 g/1 L, peptone 8 g/1 L, agar 10 g/1 L). The strains were inoculated and cultured in the produced medium, and it was confirmed that a transparent ring was formed by dropping an iodine solution used for gram-staining around the colonies of the grown strain.

③ The decomposition ability for gelatin of each strain was confirmed. Gelatin medium (12% gelatin, 20 g/1 L peptone, 10 g/1 L yeast extract, and 20 g/1 L dextrose) was solidified on 15 ml test tube. The bacteria were inoculated in the middle of the solidified gelatin medium by using platinum wire, and cultured at room temperature (20° C. to 23° C.). Whether each bacterium has the decomposition ability for gelatin was confirmed by confirming that the gelatin was decomposed and liquefied.

④ Catalase is an enzyme having heme as a prosthetic group, and is mainly present in aerobic or anaerobic bacteria having cytochrome. A catalase test is conducted by confirming whether bubbles are generated by mixing 3% (v/v) hydrogen peroxide so as to be 10 Vol % of bacterial culture broth, or by confirming whether bubbles are generated by dropping a hydrogen peroxide solution on colonies of the solid medium. Each bacterium was inoculated in a nutrient plate medium and cultured at 30° C.

Whether bubbles are generated around each bacterium was confirmed by dropping 5 µl of 3% hydrogen peroxide solution onto single colony of each bacterium.

⑤ An oxidase test is used to classify aerobic bacteria and facultative anaerobic bacteria. The oxidase test is a method confirming whether cytochrome oxidase is activated, wherein the cytochrome oxidase catalyzes a process of oxidizing reduction type cytochrome by oxygen which is a final electron acceptor of an electron transport system. Each bacterium was inoculated in a nutrient plate medium and cultured at 30° C. After a solution of a-naphthol/95% ethanol: 1% dimethyl-p-phenylenediamine oxalate solution) mixed at a ratio of 1:1 was added to each single colony of each bacterium, whether the colony represents dark blue within 10 to 30 seconds was confirmed.

6) An indole test is a method confirming whether tryptophan among amino acids is used. The bacterium was inoculated in peptone water (peptone 10 g/1 L, sodium chloride 5 g/1 L), and cultured in a 30° C. incubator, and 100 μl of Kovac solution (p-dimethylaminobenzaldehyde 3 g, butanol 75 ml, and hydrochloride (HCl) 25 ml) was added and mixed. Positive was shown as pink or red, and negative did not show a change in color.

8) Identification of Biochemical Properties using API ZYM Kit

The API ZYM kit (bioMerieux) is a kit that is mainly used to test an enzymatic activity of microorganism, and may be applied to almost every kind of strain. An activity of 19 enzymes may be rapidly confirmed with a small amount of bacterial cells, and an activity of the enzymes in a non-purified mixed sample may be confirmed. In order to confirm the extent of bacterial growth or the difference of enzyme activity shown depending on growth conditions, bacteria cultured in a rich plate medium (1% tryptone, 0.5% NaCl, 0.5% yeast extract, 0.3% beef extract, 1% agar, pH 10) and a YPD plate medium (1% yeast extract, 2% peptone, 2% dextrose, 1% agar, pH 10) were dissolved in sterile distilled water or 0.85% sodium chloride (NaCl) solution so that absorbance is 1 to 1.5 at 550 nm. 150 μl of bacterial solution was inoculated in each cupule of the kit and cultured at a 30° C. incubator for 4 hours. After culturing, a drop of each of the ZYM A solution and the ZYM B solution included in the kit was sequentially dropped, followed by reaction for 5 minutes, and the result was analyzed. In accordance with the elapse of time, whether color is formed was confirmed by reaction at room temperature for 1 hour and 12 hours.

9) Medium Optimization: Test for Carbon Source

In order to establish appropriate culture condition for reducing ability of four strains isolated from traditional fermentation solution, tests for each medium condition were performed. The most important basic component in the culture condition is carbon source. Therefore, test was conducted to find out whether the strain is grown for the carbon source and the preference therefor. 1% of carbon source was added to the M9 minimal nutrient medium. The strains were inoculated in the M9 minimal nutrient plate media (1% agar) in which glucose, xylose, maltose, sucrose, and starch with concentration of 0% and 1% were added to 100 mM sodium bicarbonate ($NaHCO_3$)/sodium carbonate ($Na_2CO_3$) solution (pH 10), respectively. The strains were cultured in a 30° C. incubator for 3 days. Whether the strain is grown was confirmed according to the elapse of culture time.

TABLE 3

| <M9 salt composition> | |
| --- | --- |
| Component | g |
| $Na_2HPO_4$ | 64 |
| $KH_2PO_4$ | 15 |
| NaCl | 2.5 |
| $NH_4Cl$ | 5 |
| DDW | 900 ml |

TABLE 4

| <M9 minimal nutrient medium composition> | |
| --- | --- |
| Component | ml |
| 5X M9 salt | 200 |
| 1M $MgSO^4$ | 2 |
| Nutrient | 20 |
| 1M $CaCl^2$ | 0.1 |
| DDW | 777.9 |
| Final Volume | 1000 |

10) Medium Optimization: Test for Organic Nitrogen Source

Plate media (1% agar) were produced by adding yeast extract, beef extract, peptone, and tryptone with concentration of 0%, 0.1%, 0.5%, 1%, and 5% to 100 mM sodium bicarbonate ($NaHCO_3$)/sodium carbonate ($Na_2CO_3$) solution (pH 10), respectively. The pH of the media was controlled within the range of 9 to 10 according to each concentration of nitrogen source components. It could be confirmed that as the concentration of the nitrogen source component was increased, change in pH was largely shown, and pH was decreased. Each strain was inoculated and cultured in a 30° C. incubator for 3 days. Whether the strain is grown was confirmed according to the elapse of time.

Results and Consideration

1) Metagenomic DNA Extraction from Indigo Fermentation Broth

The total DNA extraction from traditional fermentation broth contains a large amount of insoluble colored compounds including indigo and plant remnants, such that impurities are largely present. Therefore, in order to extract only the pure bacteria-derived DNA that is less damaged by mechanical sheer stress used in an extraction process so as not to include the impurities, the extraction methods may be changed, for example, a sample fractionation process may be performed as a preceding process, to extract DNA with high purity.

2) Amplification of 16s rRNA and Construction of Library 16s rRNA gene is a region that is well conserved in an evolutionary process, and is utilized for phylogenetic studies of prokaryotes and used for identification of microorganisms and community analysis. 16s rRNA is divided into conservation sequence and variable sequence. The conservation sequence is a base sequence commonly present and conserved in many organisms due to a structural or functional role, and the variable region is a base sequence having large diversity according to differentiation of species and genus of microorganisms and being present in only the specific group, such that it is significantly useful to identify an evolutionary relationship between microorganisms. Accordingly, when 16S rRNA gene is amplified from genomic DNA of various microorganisms extracted from the indigo fermentation broth, and inserted into a vector, and a library is constructed, various kinds of microorganisms in the indigo plant may be appreciated.

In order to construct the library, the entire 16S rRNA gene was amplified by using a universal primer bound to an indicator gene in general bacteria having the genomic DNA extracted from the indigo fermentation broth, as a template. Here, the DNA encoding a 16S rRNA has a size of about 1500 bp, which appears as a single band. However, in fact, genes derived from a number of microorganisms are mixed with each other.

The amplified 16S rRNA gene is inserted into a cloning vector to construct a library, followed by transformation into *E. coli*, and clones into which the 16S rRNA gene was inserted were screened. In the clones into which the 16S rRNA gene was introduced, whether or not the recombinant gene is inserted was confirmed by colony cracking. The resulting colony was inoculated and cultured in a liquid medium, and the recombinant plasmid was extracted.

3) Bacteria Species Analysis in Fermentation Broth through 16s rRNA Sequence Analysis When cutting the specific gene by using restriction enzyme, the specific gene is cut into various sizes of fragments by whether a recognition site of the restriction enzyme in the base sequence is present and frequency thereof. Despite being the same kind of microorganism, various patterns may be shown according to the evolutionary distance or whether mutation occurs. This process is a method that is mainly used in evolution research and strain analysis of gene, species identification, etc., in biological fields by using the above-described principle.

The extracted recombinant plasmid reacted with a cocktail enzyme solution including BamHII, EcoRI, and HindIII that are restriction enzymes recognizing and cutting six base sequences and with a restriction enzyme Sau3AI recognizing and cutting four base sequences, followed by electrophoresis. The cutting patterns were analyzed and gene clones having different patterns were screened. Consequently, 19 kinds of 16S rRNA fragment patterns were confirmed in the fermentation broth with good dyeing ability and 5 kinds of 16S rRNA fragment patterns were confirmed in the fermentation broth with poor dyeing ability from the screened total 76 gene clones, and sequences were analyzed.

1500 bp of 16S rRNA gene sequence obtained by sequence analysis was compared and analyzed with sequence of related strains by using BlastN program provided by NCBI, thereby identifying the strain in the fermentation broth. As a result, in the fermentation broth with good dyeing ability, 19 kinds of microorganisms such as ① *Alkalibacterium* sp. E-119, ② *Alkalibacterium olivoapovliticus* WW2-SN4c, ③ *Alkalibacterium psychrotolerans*, ④ Uncultured bacterium sp. SMQ95, etc., were confirmed, and in the fermentation broth with poor dyeing ability, five kinds of main microorganisms such as ① *Alkalibacterium* sp. E-119, ② Uncultured bacterium clone ambient_alkaline-56, ③ Bacterium SL3.41, etc., were confirmed. From the confirmed strains, phylogenetic relationship was confirmed by evolution system through Clustal W program using each sequence property.

As an analysis result of the 16S rRNA gene library, *Alkalibacterium* sp. was confirmed at the highest rate of 71% in the fermentation broth with good dyeing ability, and 14% of uncultured bacterium was confirmed as the second highest rate. In the fermentation broth with poor dyeing ability, about 50% of uncultured bacterium was confirmed, and about 30% of *Bacillus* sp. was confirmed. Based on the above results, it could be expected that the main strains in the fermentation broth are *Alkalibacterium* sp. and uncultured bacterium sp., and it is considered that the difference of main microflora and the difference between species found between the sample with good dyeing ability and the sample with poor dyeing ability are important reasons for providing different reducing power in the fermentation broth.

4) Search of Culture Conditions for Pure Microbial Culture and Acquisition of Strains Capable of Performing Independent Growth A test was conducted to confirm whether the species confirmed through the above results are present in the fermentation broth, and whether the species are capable of being cultured. The culture experiment was conducted by adding the composition in an LB medium to modify the medium composition. The fermentation broths were plated on the LB nutrient medium modified depending on dilution rate, and cultured at 30° C. for 4 days, and five kinds of strains having different phenotypes were separated and cultured from two fermentation broths with good dyeing ability. Then, the 16S rRNA gene was amplified through the colony PCR, and analyzed. As an analysis result of base sequence of the 16S rRNA gene, it was confirmed that the strains cultured from the fermentation broth were *Dietzia natronolimnaea* strain W5044, *Dietzia natronolimnaea* strain TPL19, *Nesterenkonia* sp. AC84, *Nesterenkonia* sp. Tibet-IBa2, *Nesterenkonia* sp. 110-8, and *Bacillus* sp. CNJ826 PL04, which were the same or similar to the corresponding strain. Some of them were strains which were not confirmed at the time of analyzing 16S rRNA gene library, and it is considered that these strains were various kinds of strains present and grown in the indigo fermentation broth.

5) New Naming of Strain Separated from with Good Dyeing Ability

In order to confirm information for four strains separated from fermentation broth and named through the preceding research, base sequence analysis was performed by amplifying the 16s rRNA gene. The 16S rRNA gene sequence obtained by PCR was compared with GeneBank Database. The strains were *Dietzia natronolimnaea* strain TPL19, *Nesterenkonia* sp. AC84, *Dietzia natronolimnaea* strain W5044, and *Nesterenkonia* sp. 110-8 named through the preceding research, which were largely classified into two genera. Through the confirmation experiment, the naming was changed by similarity of 16s rRNA gene sequence of each strain. It was confirmed that the bacterium named *Dietzia natronolimnaea* strain TPL19 had high similarity with *Dietzia natronolimnaea* strains. It was confirmed that the *Nesterenkonia* sp. AC84, the *Dietzia natronolimnaea* strain W5044, and the *Nesterenkonia* sp. 110-8, had high similarity to the *Nesterenkonia* sp. Tibet-IBa2, the *Nesterenkonia* sp. AC84, etc. It was confirmed that the 16s rRNA gene sequence of *Dietzia natronolimnaea* strain W5044 classified as other genus had high similarity to the *Nesterenkonia* sp. Similarity of the 16s rRNA gene sequence obtained by re-confirmation and the registered bacteria was confirmed, and each strain was named as new name, and registered in the GeneBank.

6) Identification of Phenotypic Properties of Strain

Through 16s rRNA gene sequence comparison, it was confirmed that strains in which sequence similarity is high were gram-positive bacteria. In order to confirm clear phenotypic properties of the four discovered strains, gram-staining was performed. It was confirmed through gram-staining that all of the four strains were gram-positive bacteria. In the gram-staining, there are some cases that gram-positive bacteria are stained as a gram-negative bacterium, such that there is often false-negative. In anaerobic bacteria, there is a more frequent possibility in which the gram-positive bacteria are discolored as gram-negative as compared to other bacteria, and there is a case in which the gram-positive bacteria are discolored as a negative even by culture conditions, such that there is difficulty in the obtaining reproducible result. Therefore, the KOH test was performed to overcome these concerns. The time at which viscosity is shown and the degree thereof were confirmed by mixing the discovered four strains with 3% KOH solution. In the KOH test, the result that strong viscosity is shown within 15 seconds is determined as gram-negative strain. The strains used for the experiment did not have viscosity. Therefore, it was confirmed that four strains were included in the gram-positive strain as confirmed with 16s rRNA sequence similarity.

7) Biochemical Properties Analysis of Strains

For accurate identification of strains, a more experiment was further attempted to provide evidences by confirming biochemical properties as well as a phenotype. A determination test capable of confirming whether each strain reacts with a specific reagent was conducted based on properties in which the strains are grown under alkaline of pH 9 or more, and the biochemical properties of the strains were confirmed by the API ZYM kit. All of the four isolated strains were gram-positive bacteria, and specific colony colors showing each phenotype were confirmed. Each bacterium in Table 6 showed different specific phenotype. It was confirmed from the gram-staining results and the KOH test that all of the isolated strains were gram-positive bacteria. As a result of a biochemical property test, in indole and catalase tests, all of the four strains were determined to have an activity, and in decomposition ability for gelatin and casein, all of the four strains were determined to have no activity. The *Dietzia* sp. KDB1, and the *Nesterenkonia* sp. KDB2, the *Nesterenkonia* sp. KDB3, the *Nesterenkonia* sp. KDB4 had different results. It was confirmed that the *Nesterenkonia* sp. KDB2, the *Nesterenkonia* sp. KDB3 and the *Nesterenkonia* sp. KDB4 had different phenotypes, but similar biochemical properties.

TABLE 6

<Test for biochemical properties of strains>

| | *Dietzia* sp. KDB1 | *Nesterenkonia* sp. KDB2 | *Nesterenkonia* sp. KDB3 | *Nesterenkonia* sp. KDB4 |
|---|---|---|---|---|
| Colony pigmentation | Red | White | Light red | Yellow |
| Gram reaction | + | + | + | + |
| KOH test | − | − | − | − |
| Oxidase test | − | + | + | + |
| Catalase test | + | + | + | + |
| Gelatin hydrolysis | − | − | − | − |
| Casein hydrolysis | − | − | − | − |
| Starch hydrolysis | − | − | − | − |
| Indole test | + | + | + | + |

(+: Positive, −: Negative)

TABLE 7

<Analysis for biochemical properties using API ZYM kit>

| | *Dietzia* sp. KDB1 | *Nesterenkonia* sp. KDB2 | *Nesterenkonia* sp. KDB3 | *Nesterenkonia* sp. KDB4 |
|---|---|---|---|---|
| Alkaline phosphatase | + | + | + | + |
| Esterase (C4) | + | + | + | + |
| Esterase lipase (C8) | + | + | + | + |
| Lipase (C14) | + | − | − | + |
| Leucinearylamidase | + | + | + | + |
| Valinearylamidase | + | + | + | + |
| Crystinearylamidase | + | − | + | + |
| Trypsin | − | + | + | + |
| a-chymotrypsin | − | − | + | + |
| acid phosphatase | + | + | + | + |
| Naphtol-AS-BI-phosphohydrolase | + | + | + | + |
| α-galactosidase | − | − | − | − |
| β-galactosidase | − | − | − | − |
| β-glucuronidase | − | − | − | − |
| α-glucosidase | + | + | + | + |
| β-glucosidase | + | − | − | − |
| N-acetyl-β-glucosaminidase | − | − | − | − |
| α-mannosidase | − | − | − | + |
| α-fucosidase | − | − | − | − |

(+: Positive, −: Negative)

As a result of the API ZYM kit, the *Nesterenkonia* sp. KDB2, the *Nesterenkonia* sp. KDB3 and the *Nesterenkonia* sp. KDB4 had similar properties to each other, but the *Dietzia* sp. KDB1 had different properties from these three strains. All of the four strains did not have activity to α-galactosidase, β-galactosidase, β-glucuronidase, and α-fucosidase, and from these results, information for carbon source to be used in the medium could be obtained.

8) Medium Optimization of Strain

In order to establish the culture conditions of the strain, whether the carbon source and the nitrogen source are utilized was confirmed under an alkaline condition. The M9 minimal nutrient media in 100 mM $NaHCO_3/Na_2CO_3$ solution (pH 10.04) were produced and 1% carbon source was added thereto. Glucose, xylose, maltose, sucrose, and starch with concentration of 1% were added to the media, respectively, and cultured in a 30° C. incubator for 3 days. All strains were not grown in the control group medium in which the carbon source was not added (0%), and were not grown even in the media including 1% glucose, 1% xylose, 1% maltose, 1% sucrose, and 1% starch, respectively. Based on the matter that the carbon source was not included in the composition of the rich medium used in the related art study, and that the strains were not grown in the minimal nutrient medium including the carbon source, it was expected that four kinds of isolated strains did not use the carbon sources such as glucose, xylose, maltose, sucrose, starch, etc., as the main energy source. The rich medium that has been used so far mainly consists of organic nitrogen sources such as yeast extract, beef extract, and tryptone. The strains were capable of being generally grown in the media including a large amount of organic nitrogen sources even though the growth degree varied depending on the pH. Therefore, plate media were produced based on 100 mM sodium bicarbonate ($NaHCO_3$)/sodium carbonate ($Na_2CO_3$) solution (pH 10.04) with the frequently used organic nitrogen sources. The pH of the media was controlled within the range of 9 to 10 according to each concentration of nitrogen sources (0, 0.1, 0.5, 1 and 5%), and as the concentration of the nitrogen source was increased, pH was decreased. All strains were capable of being grown by the yeast extract even with low concentration as 0.1%, and colonies and specific color of the strains were clearly shown by 1% yeast extract. In the beef extract (5%), three *Nesterenkonia* sp. strains except for the *Dietzia* sp. KDB1 strain were grown with clear phenotype. The *Dietzia* sp. KDB1 strain was capable of being grown by beef extract, but specific red colonies were not clearly formed. In the medium including 1% peptone, all strains were grown having a faint color, and in the medium including 5% peptone, all strains were grown having clear colors while forming colonies. In the medium including 1% tryptone, three *Nesterenkonia* sp. strains were grown with unclear phenotype, and the *Dietzia* sp. KDB1 strain was grown with clear red colonies, which was opposite to the results of the beef extract. In the medium including 5% tryptone, the *Dietzia* sp. KDB1 was actively grown, but three *Nesterenkonia* sp. strains were slowly grown as compared to the medium including 1% tryptone.

TABLE 8

<Confirmation whether strains are grown by organic nitrogen source>

| Nutrient | *Dietzia* sp. KDB1 | *Nesterenkonia* sp. KDB2 | *Nesterenkonia* sp.KDB3 | *Nesterenkonia* sp.KDB4 |
|---|---|---|---|---|
| Yeast extract | + | + | + | + |
| Beef extract |   | + | + | + |
| Peptone | + | + | + | + |
| Tryptone | + |   |   |   |

(+: strain capable of being grown having clear phenotype)

Reducing Power Evaluation Test of New Strains

1) Strain Culture and Quantification

The strain suspension cultured at optimal culture condition was taken and the strain was allowed to be precipitated by using a centrifuge (1580MGR, Gyrozen Co., Ltd, Korea) (12000 rpm, 1 min, 4), and the resulting strain was directly used for indigo reduction. The cell mass of the cultured broth was confirmed with an optical density (O.D.) at 600 nm by using UV absorptiometer (Agilent 845, Agilent Technologies, Waldbronm, Germany), and the final optical density was 1.8 to 2.0. Provided that the used bacterial strain amount was provided as a quantitative value (dry weight) obtained by fully drying the strain obtained by centrifugation in an oven.

2) Reducing Power Evaluation

The reduction was performed in 32° C. incubator by using indigo (natural indigo 2.5 g, synthetic indigo 0.25 g) sterilized under high temperature and high pressure (120° C., minutes) in a filtered 0.2% sodium carbonate aqueous solution (pH 11.32, 35 mL). As the natural indigo, indigo plant grown in Naju, Jeollanam-do Province, was used with slaked lime to precipitate pigment, thereby making an indigo paste, and then a drying process was performed in a 50° C. oven to prepare powder dye (indigo 10.66% (W/W)), and the synthetic indigo was a commercially available product (Indigo, Vat Blue 1, Aldrich, Germany).

In order to observe the reduction degree, the bacterial strain (7-100 mg) was added to the above-described reducing solution, and ramie fabric dyeing was performed according to the elapse of time. The ramie fabric sample was immersed in the supernatant of the reducing solution for 20 minutes, followed by oxidation in air, color development, and washing, and then, the dyed ramie fabric sample was neutralized in 0.1% acetic acid aqueous solution for 10 minutes, and washed and dried. In addition, before the dyeing, pH of the reducing solution was measured.

3) Measurement of Dye Uptake and Color Characteristic

Surface dye uptake of the dyed fabric was evaluated as K/S values at the maximum absorption wavelength by using a colorimeter (Color-Eye 3100, Macbeth, USA), and the color characteristic was measured as H V/C values of Munsell.

Reducing Power Evaluation Result of New Strains

1) Indigo Reduction Using *Dietzia* sp. KDB 1

Natural Indigo Reduction

Figure 2A:
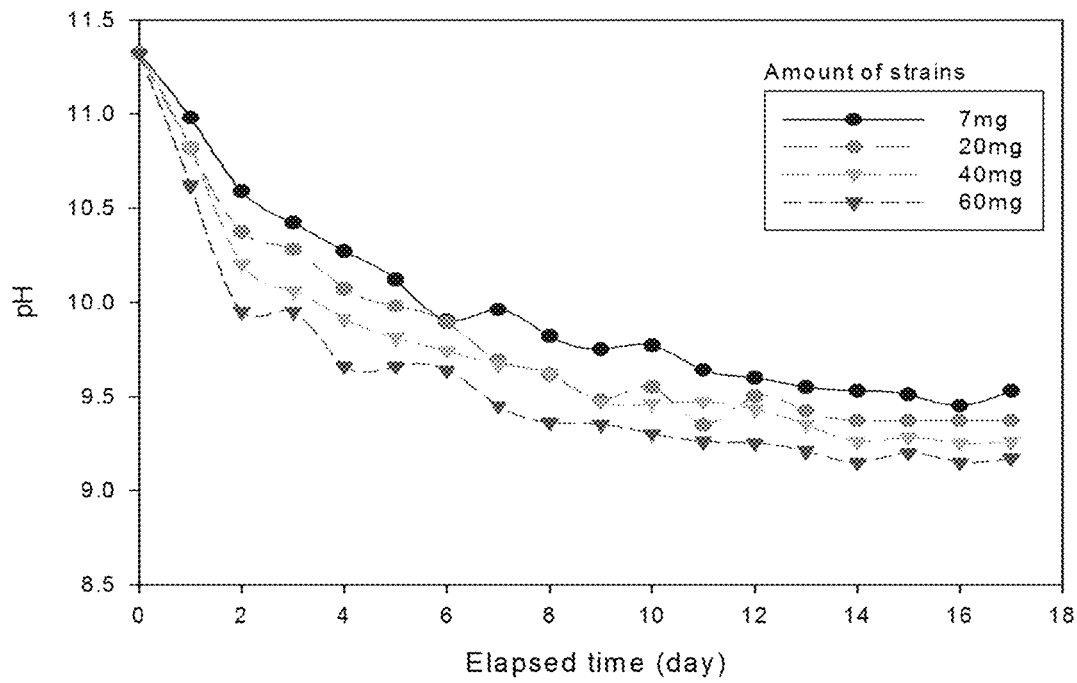
FIGS. 2A and 2B each show (a) pH change and (b) K/S change depending on elapsed days when reducing natural indigo by *Dietzia* sp. KDB1.
Figure 2B:
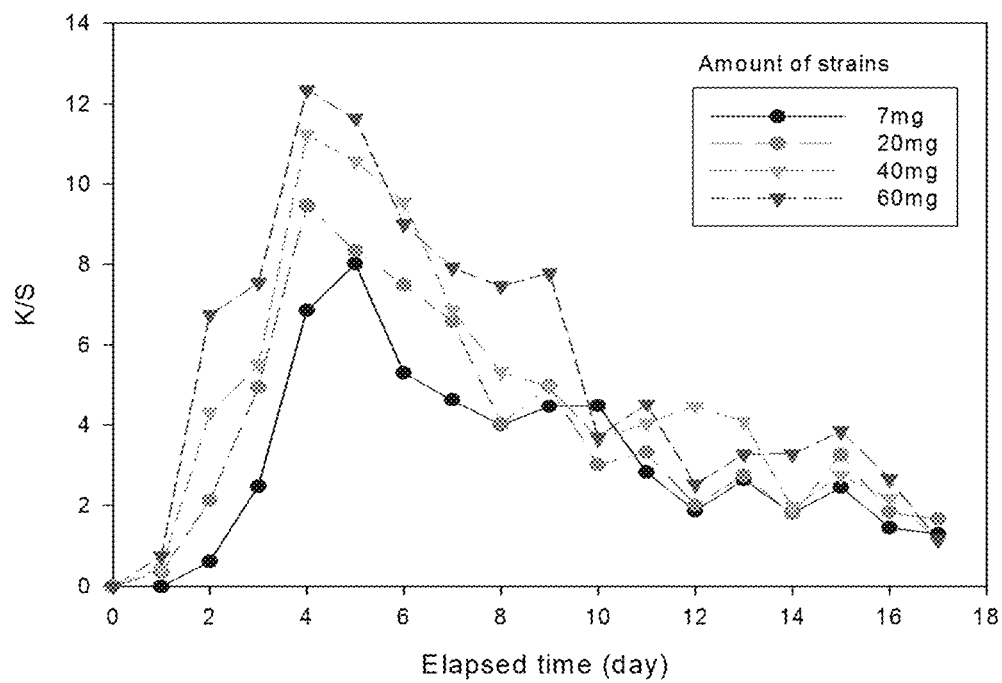

The pH of the reducing solution and change in dye uptake depending on the reduction elapsed time when reducing natural indigo by using the bacterial strain *Dietzia* sp. KDB1 were shown in FIG. 2. It could be appreciated that the pH was continuously reduced as time elapsed regardless of the strain amount, and as the strain amount was increased, the degree of pH reduction depending on the elapsed time was increased, such that the pH value was lower at the same elapsed time. In the dye uptake, K/S values were continuously increased up to the day having maximum dye uptake regardless of the strain amount, and gradually decreased afterward. At the same elapsed time, as the strain amount was increased, higher K/S value was shown up to the day having maximum dye uptake, but afterward, the large strain amount was not necessarily shown with high K/S value.

The pH of dye bath, K/S values and H V/C values of the dyed fabric on the day reduction is initiated, and the reduction day having the maximum dye uptake when reducing natural indigo depending on strain amounts, were shown in Table 9. When reducing the indigo by adding 7 mg of strain, the reduction dyeing was shown on Day 2, and when reducing the indigo by adding 20 mg, 40 mg, and 60 mg of strains, the reduction dyeing was shown immediately after Day 1. As described above, the reduction initiation rapidly progressed when adding the strain, but the initial dye uptake according to the addition of strain was 0.37 to 0.75, and accordingly, significant difference was not shown. All cases had PB-series colors. When adding 7 mg of strain, the maximum dye uptake was shown on Day 5, and when adding 20 mg, 40 mg, and 60 mg of strain, all of the maximum dye uptake were shown on Day 4. Therefore, regardless of the addition of strain, the reduction was initiated, and the maximum dye uptake was shown after Day 3 in all cases. Respective K/S values were 3.83, 8.02, 9.47, 11.23, and 12.35, and as the strain addition amount was increased, higher K/S value was shown, wherein the pH of the dye bath was lower as the strain addition amount was increased. All of the dyed fabrics had PB-series colors, and as the strain addition amount was increased, the fabrics were dyed with PB-series color close to purple. As the strain addition amount was increased, the brightness and saturation values were continuously decreased, a darker and turbid color was shown, which is because the K/S value was higher as the strain addition amount was increased.

TABLE 9

| <Natural indigo reduction by *Dietzia* sp. KDB 1> | | | | | | | | |
|---|---|---|---|---|---|---|---|---|
| | Reduction Initiation | | | | Maximum dye uptake | | | |
| Strain amount (mg) | Elapsed days | pH | K/S value | H V/C | Elapsed days | pH | K/S value | H V/C |
| 7 | 2 | 10.59 | 0.61 | 3.4PB 6.9/3.7 | 5 | 10.12 | 8.02 | 3.5PB 3.7/5.0 |
| 20 | 1 | 10.82 | 0.37 | 2.6PB 7.6/2.7 | 4 | 10.07 | 9.47 | 4.0PB 3.4/4.8 |
| 40 | 1 | 10.82 | 0.45 | 2.5PB 7.3/3.0 | 4 | 9.91 | 11.23 | 4.3PB 3.1/4.4 |
| 60 | 1 | 10.62 | 0.75 | 3.3PB 6.6/3.9 | 4 | 9.66 | 12.35 | 4.4PB 2.9/4.1 |

Synthetic Indigo Reduction

Figure 3A:
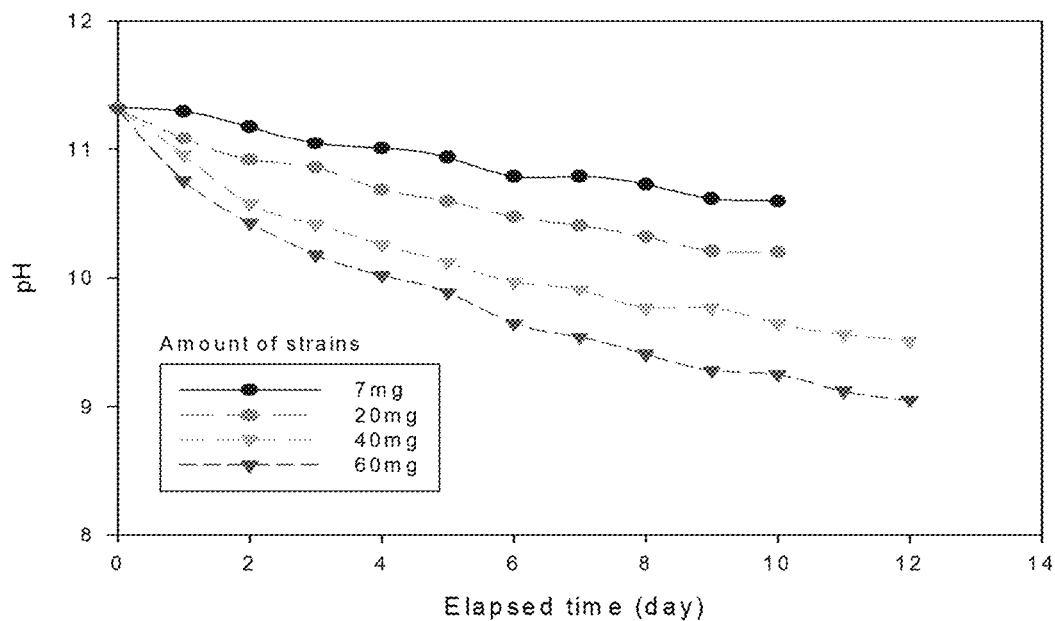
FIGS. 3A and 3B each show (a) pH change and (b) K/S change depending on elapsed days when reducing synthetic indigo by the *Dietzia* sp. KDB1.
Figure 3B:
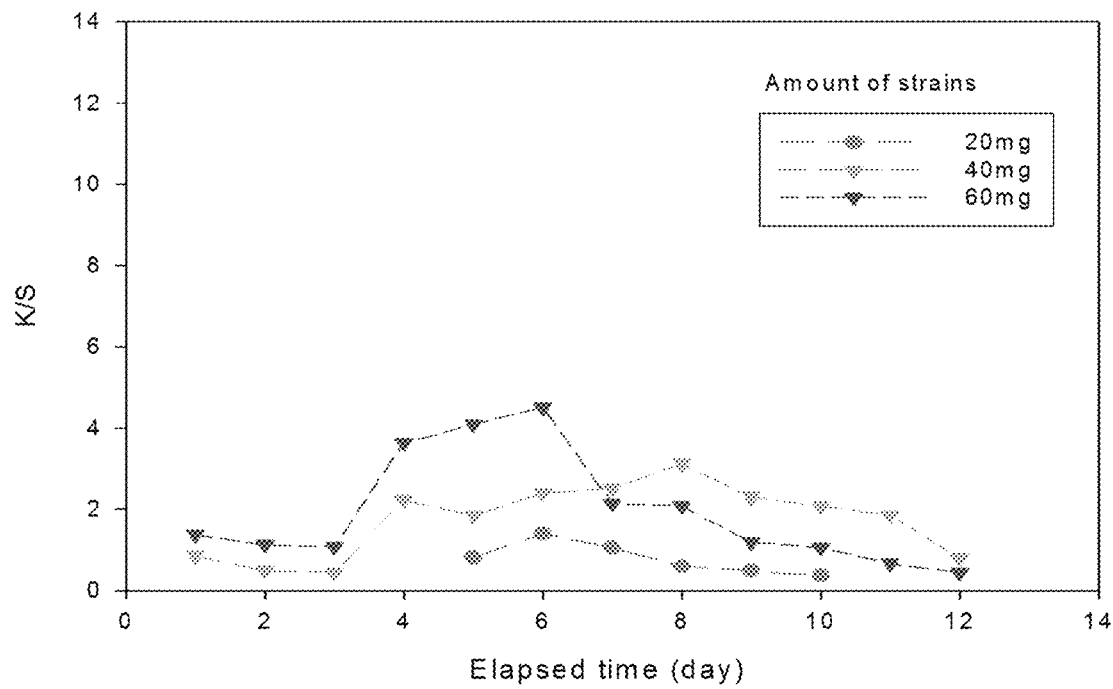

The pH of the reducing solution and change in dye uptake depending on reduction elapsed time when reducing synthetic indigo by using the bacterial strain *Dietzia* sp. KDB1 were shown in FIG. 3. The pH was continuously reduced as time elapsed regardless of the strain amount, and as the strain amount was increased, the degree of pH reduction depending on the elapsed time was increased, such that the pH value was lower at the same elapsed time. In the dye uptake, when adding 7 mg of strain, the reduction was not shown, and when adding 20 mg to 60 mg of strain, as the strain amount was increased, the K/S value was higher until Day 6, and from Day 7, the case of adding 40 mg of strain had higher K/S value than the case of adding 60 mg of strain.

The pH of dye bath, K/S values and H V/C values of the dyed fabric at the day reduction is initiated, and the reduction day having the maximum dye uptake when reducing synthetic indigo depending on strain amounts, were shown in Table 10, except for the case in which the reduction was not shown. When adding 20 mg of strain, the reduction was shown on Day 5, and the next day, the maximum dye uptake (K/S value was 1.39) was shown, and from Day 8, the K/S value was 1 or less. When adding 40 mg and 60 mg of strain, the reduction was shown in one day, but in the case of adding 60 mg of strain, a two times larger initial dye uptake than that of the case of adding 40 mg of strain was shown. In addition, it could be confirmed that as the strain amount was increased, the maximum dye uptake was higher. Here, the pH of dye bath was lower as the strain addition amount was increased, all were dyed with PB-series color. In addition, as the strain addition amount was increased, brightness was low and saturation was high, a dark but clear color was shown.

time elapsed regardless of the strain amount, and as the strain amount was increased, the degree of pH reduction depending on the elapsed time was increased, such that the pH value was lower at the same elapsed time. In the dye uptake, as the strain amount was increased, the dye uptake was high at the same elapsed time, but in 7 mg, 20 mg and 40 mg of strain amounts, the difference in dye uptake according to the strain amount was not significant. In 7 mg of strain amount, the reduction dyeing was shown until Day 5, and in 20 mg, 40 mg, and 60 mg of strain amounts, the reduction dyeing was shown until Day 7, 10, and 14. As the strain amount was increased, reducing power was maintained longer, but K/S value was significantly low.

The pH of dye bath, K/S values and H V/C values of the dyed fabric on the day reduction is initiated, and the reduction day having the maximum dye uptake when reducing natural indigo depending on strain amounts, were shown in Table 11. When reducing the indigo by adding 7 mg and 20 mg of strain, the reduction dyeing was shown on Day 3, and when reducing the indigo by adding 40 mg and 60 mg of strains, the reduction dyeing was shown on Day 2. The initial dye uptake according to the addition of strain was 0.34 to 0.39 in 7 mg, 20 mg, and 40 mg of strain, and the initial dye uptake was the highest value as 1.14 in 60 mg of strain. All cases were dyed with PB-series colors. When adding 7 mg of strain, the maximum dye uptake was shown on Day 4, when adding 20 mg of strain, the maximum dye uptake was shown on Day 5, and when adding 40 mg and 60 mg of strains, the maximum dye uptake was shown on Day 3. Respective K/S values were 0.42, 0.82, 1.01, and 2.65, and as the strain addition amount was increased, the K/S value was slightly higher, wherein the pH of the dye bath was 9.50 to 9.69, and accordingly, significant difference was

TABLE 10

<Synthetic indigo reduction by *Dietzia* sp. KDB 1>

| Strain amount (mg) | Reduction Initiation | | | | Maximum dye uptake | | | |
|---|---|---|---|---|---|---|---|---|
| | Elapsed days | pH | K/S value | H V/C | Elapsed days | pH | K/S value | H V/C |
| 20 | 5 | 10.60 | 0.81 | 2.3PB 6.8/3.5 | 6 | 10.48 | 1.39 | 2.2PB 6.2/4.1 |
| 40 | 1 | 10.96 | 0.85 | 3.2PB 7.0/3.5 | 8 | 9.77 | 3.12 | 3.1PB 5.0/4.5 |
| 60 | 1 | 10.75 | 1.36 | 3.2PB 6.3/4.5 | 6 | 9.65 | 4.51 | 3.0PB 4.7/5.3 |

2) Indigo Reduction Using *Nesterenkonia* sp. KDB2

Natural Indigo Reduction

Figure 4A:
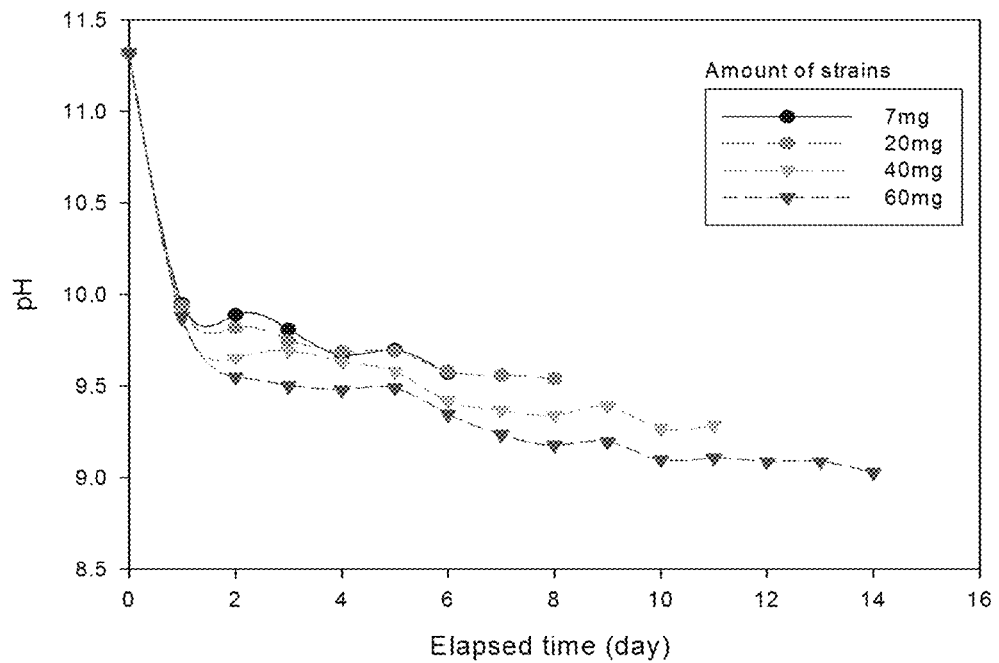
FIGS. 4A and 4B each show (a) pH change and (b) K/S change depending on elapsed days when reducing natural indigo by *Nesterenkonia* sp. KDB2.
Figure 4B:
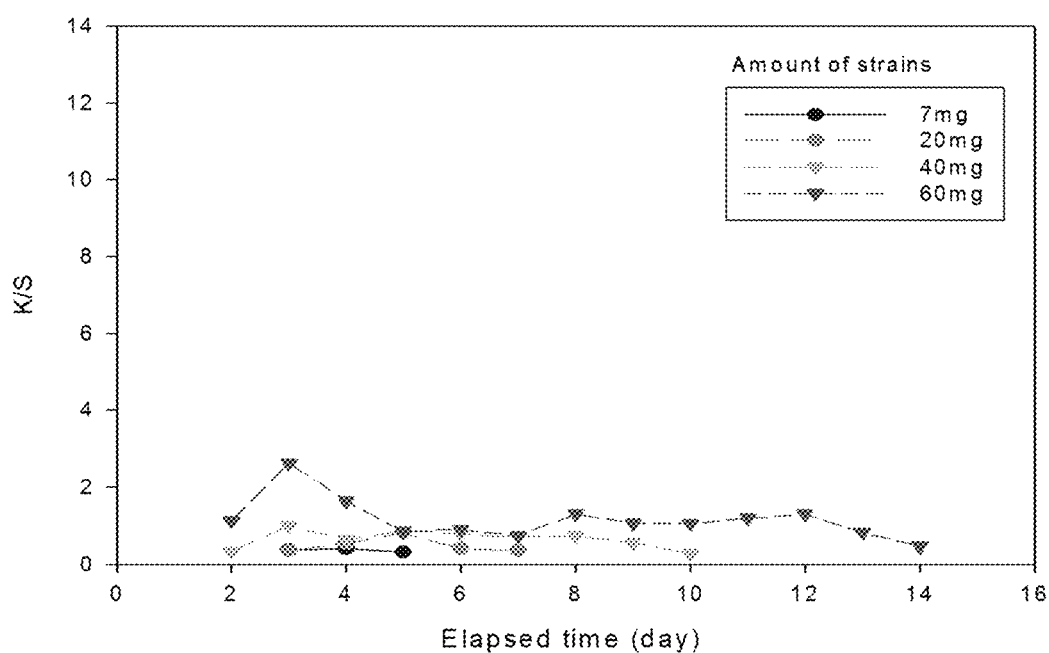

The pH of the reducing solution and change in dye uptake depending on reduction elapsed time when reducing natural indigo by using the bacterial strain *Nesterenkonia* sp. KDB2 were shown in FIG. 4. The pH was continuously reduced as not shown according to the strain addition amount. All of the dyed fabrics had PB-series colors, and as the strain addition amount was increased, the fabrics were dyed with PB-series color close to blue. As the strain addition amount was increased, the brightness was continuously decreased, and the saturation values were continuously increased, such that the fabrics were dyed with darker, but clear colors.

TABLE 11

<Natural indigo reduction by *Nesterenkonia* sp. KDB 2>

| Strain amount (mg) | Reduction Initiation | | | | Maximum dye uptake | | | |
|---|---|---|---|---|---|---|---|---|
| | Elapsed days | pH | K/S value | H V/C | Elapsed days | pH | K/S value | H V/C |
| 7 | 3 | 9.81 | 0.39 | 0.4PB 7.5/2.8 | 4 | 9.67 | 0.42 | 3.5PB 7.4/3.3 |
| 20 | 3 | 9.75 | 0.36 | 2.2PB 7.5/3.0 | 5 | 9.69 | 0.82 | 3.2PB 6.6/4.0 |

TABLE 11-continued

<Natural indigo reduction by *Nesterenkonia* sp. KDB 2>

| Strain amount (mg) | Reduction Initiation | | | | Maximum dye uptake | | | |
|---|---|---|---|---|---|---|---|---|
| | Elapsed days | pH | K/S value | H V/C | Elapsed days | pH | K/S value | H V/C |
| 40 | 2 | 9.65 | 0.34 | 2.1PB 7.6/2.5 | 3 | 9.69 | 1.01 | 2.5PB 6.4/4.1 |
| 60 | 2 | 9.55 | 1.14 | 2.6PB 6.4/4.5 | 3 | 9.50 | 2.65 | 2.3PB 5.2/4.9 |

Synthetic Indigo Reduction

Figure 5A:
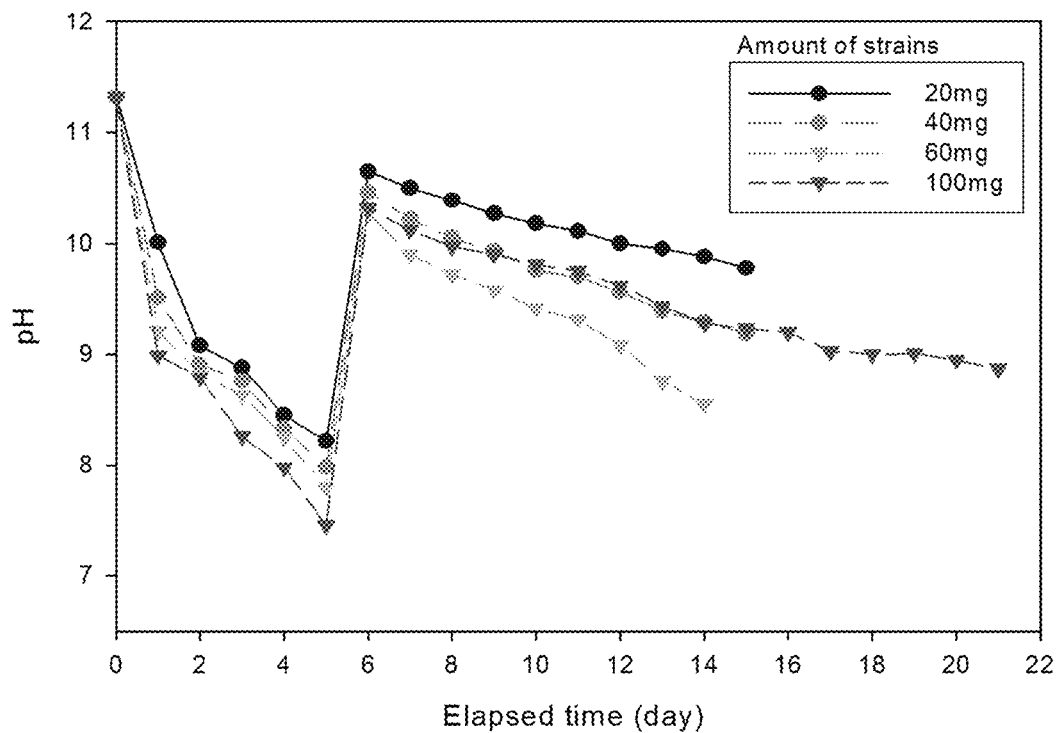
FIGS. 5A and 5B each show (a) pH change and (b) K/S change depending on elapsed days when reducing synthetic indigo by the *Nesterenkonia* sp. KDB2.
Figure 5B:
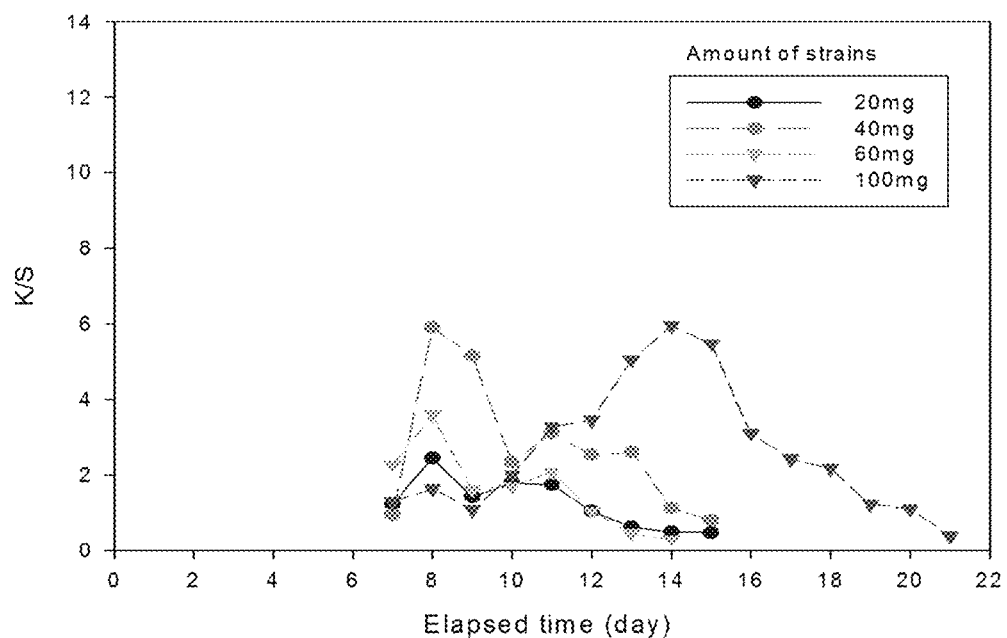

The pH of the reducing solution and change in dye uptake depending on reduction elapsed time up to the reduction end day when reducing synthetic indigo by using the bacterial strain *Nesterenkonia* sp. KDB2 were shown in FIG. 5. The strain amounts were 20 mg, 40 mg, 60 mg, and 100 mg. The pH was rapidly reduced as time elapsed regardless of the strain amount, and on Day 6, pH was controlled to 10.30 to 10.65 by adding $Na_2CO_3$ (20 to 60 mg of strain: 0.05 g, 100 mg of strain: 0.10 g). Until 60 mg of strain, as the strain amount was increased, the pH reduction depending on the elapsed time was increased, such that the pH value was lower at the same elapsed time.

However, in 100 mg of strain, the alkaline addition amount was slightly increased at the time of controlling the pH, such that change in pH in 100 mg of strain was similar to that in 40 mg of strain. In the dye uptake, the reduction dyeing was initiated after pH control by the alkaline addition regardless of the strain amount, and the constant tendency according to the strain addition amount was not shown. Until Day 10, the dye uptake was increased in a sequence of 40 mg, 60 mg, 20 mg, and 100 mg, and after Day 10, the dye uptake was the highest in 100 mg, and the second-highest in 40 mg, and the dye uptakes of 20 mg and 60 mg were almost similar to each other and the lowest. The reducing power was maintained longer in 100 mg in which the strain addition amount was the largest.

The pH of dye bath, K/S values and H V/C values of the dyed fabric on the day reduction is initiated, and the reduction day having the maximum dye uptake of the synthetic indigo depending on the strain amounts, were shown in Table 12. Regardless of the strain amount, in 20 mg, 40 mg, 60 mg, and 100 mg of strains, the reduction was shown on Day 7 which was the next day after controlling the pH by adding alkaline, and the maximum dye uptakes of 20 mg, 40 mg, 60 mg of strain were 2.46, 5.92 and 3.61 on Day 8, respectively, and after Day 8, the maximum dye uptakes were decreased. In 100 mg of strain, the maximum dye uptake (5.96) was shown with the similar value as 40 mg of strain on Day 14, which was 6 days later as compared to other strain amounts. All cases were dyed with PB-series colors. In samples dyed with 40 mg and 100 mg of strains in which the maximum dye uptakes are similar to each other, brightness and saturation of the sample dyed with 100 mg of strain were higher.

TABLE 12

<Synthetic indigo reduction by *Nesterenkonia* sp. KDB 2>

| Strain amount (mg) | Reduction Initiation | | | | Maximum dye uptake | | | |
|---|---|---|---|---|---|---|---|---|
| | Elapsed days | pH | K/S value | H V/C | Elapsed days | pH | K/S value | H V/C |
| 20 | 7 | 10.50 | 1.23 | 2.5PB 6.1/3.8 | 8 | 10.39 | 2.46 | 3.0PB 5.5/5.0 |
| 40 | 7 | 10.22 | 0.95 | 2.3PB 6.5/3.2 | 8 | 10.05 | 5.92 | 3.7PB 3.9/4.3 |
| 60 | 7 | 9.90 | 2.28 | 2.6PB 5.7/4.6 | 8 | 9.72 | 3.61 | 3.0PB 5.0/5.4 |
| 100 | 7 | 10.12 | 1.31 | 2.6PB 6.0/4.0 | 14 | 9.28 | 5.96 | 3.1PB 4.3/5.2 |

3) Indigo Reduction using *Nesterenkonia* sp. KDB3

Natural Indigo Reduction

Figure 6A:
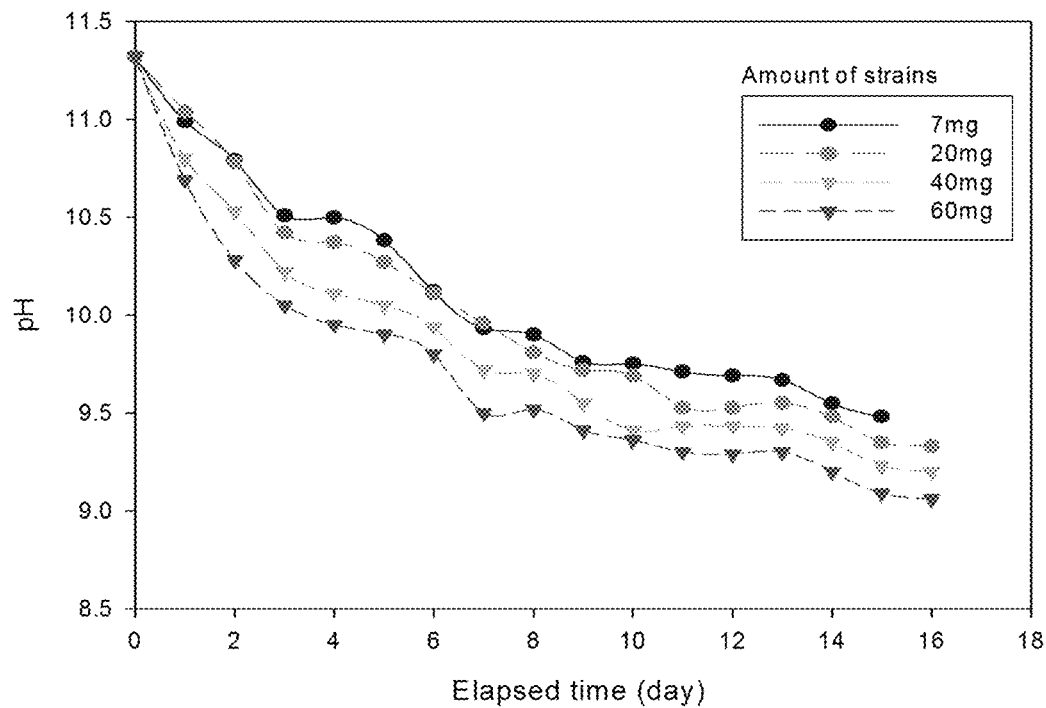
FIGS. 6A and 6B each show (a) pH change and (b) K/S change depending on elapsed days when reducing natural indigo by *Nesterenkonia* sp. KDB3.
Figure 6B:
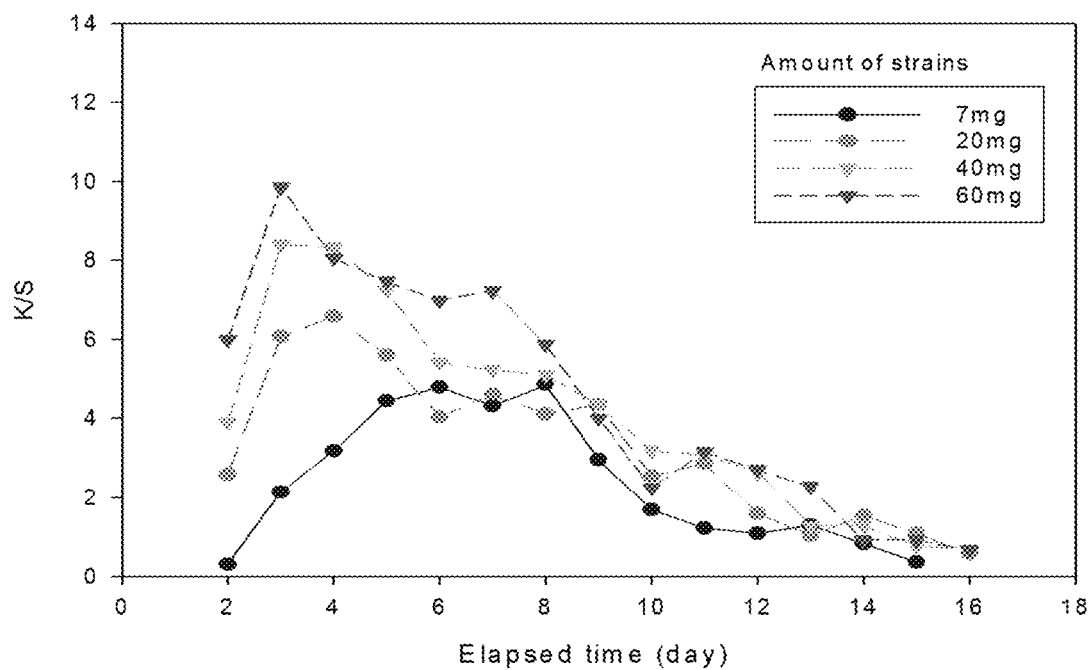

The pH of the reducing solution and change in dye uptake depending on reduction elapsed time when reducing natural indigo by using the bacterial strain *Nesterenkonia* sp. KDB3 were shown in FIG. 6. The pH was continuously reduced as time elapsed regardless of the strain amount, and as the strain amount was increased, the degree of pH reduction depending on the elapsed time was increased, such that the pH value was lower at the same elapsed time. The dye uptake was decreased after the day having maximum dye uptake regardless of the strain amount, and the large strain amount was not necessarily shown with high K/S value. The reducing power was similarly maintained until about Day 15 to 16 without a significant difference according to a strain amount.

The pH of the dye bath, K/S values and H V/C values of the dyed fabric on the day reduction is initiated, and the reduction day having the maximum dye uptake when reducing natural indigo depending on strain amounts, were shown in Table 13. In all cases regardless of the strain amounts, the reduction dyeing was shown on Day 2, and the initial dye uptakes were 0.32, 2.59, 3.90, and 5.99, respectively, and as the strain amount was increased, the K/S value was higher. All had PB-series colors. When adding 7 mg of strain, the maximum dye uptake was shown on Day 6, and when adding 20 mg of strain, the maximum dye uptake was shown on Day 4. When adding 40 mg and 60 mg of strain, all of the maximum dye uptakes were shown on Day 3. Respective K/S values were 4.81, 6.59, 8.40, and 9.86, and as the strain amount was increased, the maximum dye uptake was higher. All of the dyed fabrics had PB-series colors, and as the strain addition amount was increased, the fabrics were dyed with PB-series color close to purple. As the strain addition amount was increased, the brightness was decreased. In 20 mg of strain, the saturation was increased by about 0.1, but afterward, the saturation was decreased, such that as the strain addition amount was increased, a darker and turbid color was shown.

TABLE 13

<Natural indigo reduction by *Nesterenkonia* sp. KDB 3>

| Strain amount (mg) | Reduction Initiation | | | | Maximum dye uptake | | | |
| --- | --- | --- | --- | --- | --- | --- | --- | --- |
| | Elapsed days | pH | K/S value | H V/C | Elapsed days | pH | K/S value | H V/C |
| 7 | 2 | 10.79 | 0.32 | 3.1PB 7.4/2.5 | 6 | 10.12 | 4.81 | 3.2PB 4.4/5.4 |
| 20 | 2 | 10.78 | 2.59 | 3.2PB 5.3/5.0 | 4 | 10.37 | 6.59 | 3.6PB 4.0/5.5 |
| 40 | 2 | 10.53 | 3.90 | 3.2PB 4.7/5.3 | 3 | 10.22 | 8.40 | 3.7PB 3.6/5.2 |
| 60 | 2 | 10.27 | 5.99 | 3.3PB 4.3/5.4 | 3 | 10.05 | 9.86 | 3.9PB 3.4/4.9 |

Synthetic Indigo Reduction

Figure 7A:
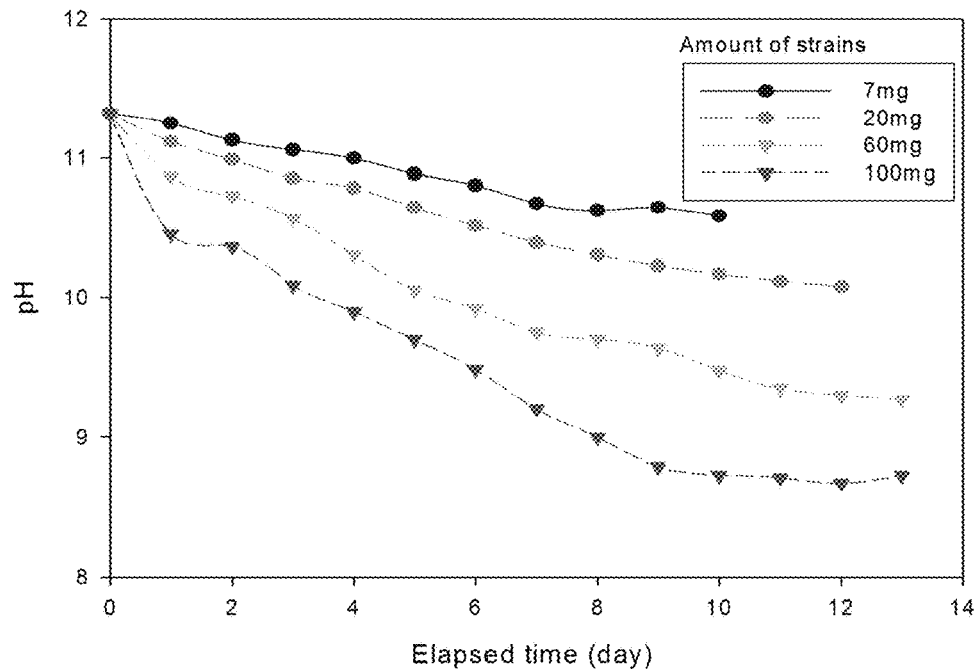
FIGS. 7A and 7B each show (a) pH change and (b) K/S change depending on elapsed days when reducing synthetic indigo by the *Nesterenkonia* sp. KDB3.
Figure 7B:
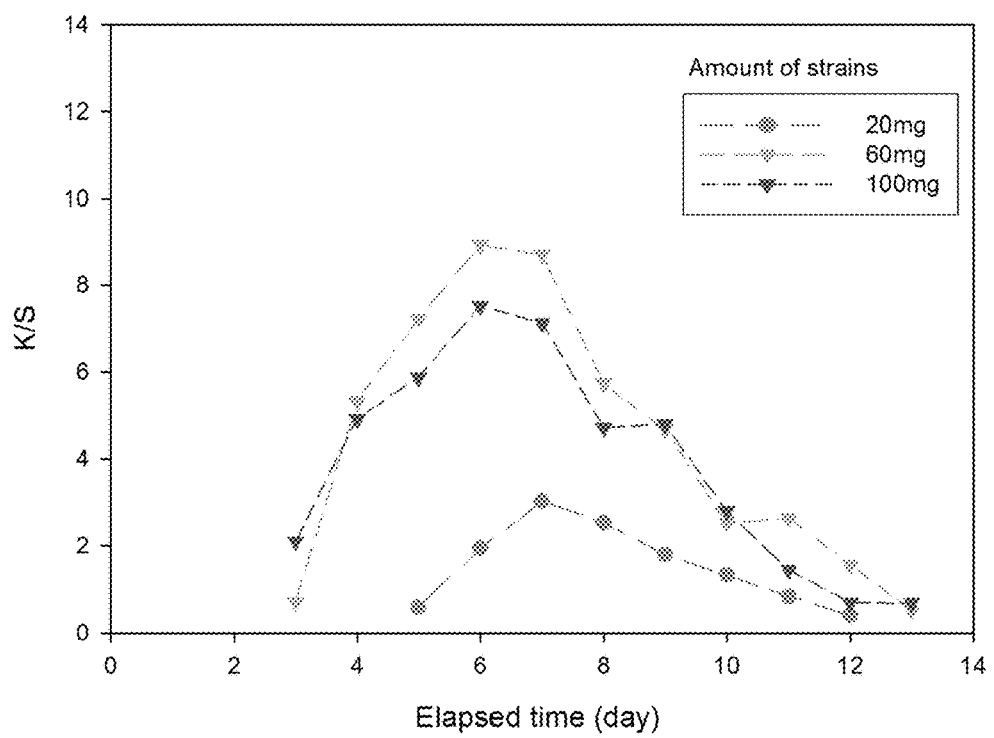

The pH of the reducing solution and change in dye uptake depending on reduction elapsed time up to the reduction end day when reducing synthetic indigo by using the bacterial strain *Nesterenkonia* sp. KDB3 were shown in FIG. 7. The strain amounts were 7 mg, 20 mg, 60 mg, and 100 mg. The pH was continuously reduced as time elapsed in all strain amounts, and as the strain amount was increased, the degree of pH reduction depending on the elapsed time was significantly large, such that the pH value was lower at the same elapsed time. In the dye uptake, when adding 7 mg of strain, the reduction was not shown, and when adding 20 mg, 60 mg and 100 mg of strains, as the strain amount was increased, the K/S value was higher until Day 10, except for Day 2 on which the reduction was initiated, but after Day 10, the case of adding 60 mg of strain had higher K/S value than the case of adding 100 mg of strain. The reducing power was shown until about Day 12 to 13, which was similar to each other according to strain amount.

The pH of dye bath, K/S values and H V/C values of the dyed fabric at the day reduction is initiated, and the reduction day having the maximum dye uptake when reducing synthetic indigo depending on strain amounts, were shown in Table 14, except for 7 mg of strain amount in which the reduction was not shown. When adding 20 mg of strain, the reduction was shown on Day 5, and the maximum dye uptake (K/S value was 3.04) was shown on Day 7, and the dye uptake was continuously decreased. When adding 60 mg and 100 mg of strain, the reduction was shown on Day 3, and the maximum dye uptake was shown on Day 6. The K/S value was higher in 100 mg of strain at the reduction initiation, but the maximum dye uptake was slightly higher in 60 mg of strain. The pH of dye bath showing the maximum dye uptake was lower as the strain addition amount was increased. All cases had PB-series colors, and as the maximum dye uptake was increased, the brightness was lower, and the saturation was the same as each other or lower.

TABLE 14

<Synthetic indigo reduction by *Nesterenkonia* sp. KDB 3>

| Strain amount (mg) | Reduction Initiation | | | | Maximum dye uptake | | | |
|---|---|---|---|---|---|---|---|---|
| | Elapsed days | pH | K/S value | H V/C | Elapsed days | pH | K/S value | H V/C |
| 20 | 5 | 10.65 | 0.59 | 3.4PB 7.3/3.1 | 7 | 10.40 | 3.04 | 3.4PB 5.2/5.1 |
| 60 | 3 | 10.57 | 0.71 | 3.1PB 6.9/3.1 | 6 | 9.92 | 8.93 | 3.8PB 3.5/4.8 |
| 100 | 3 | 10.09 | 2.11 | 3.1PB 5.6/4.6 | 6 | 9.49 | 7.53 | 3.2PB 3.9/5.1 |

4) < Indigo Reduction by *Nesterenkonia* sp. KDB4 >

Natural Indigo Reduction

Figure 8A:
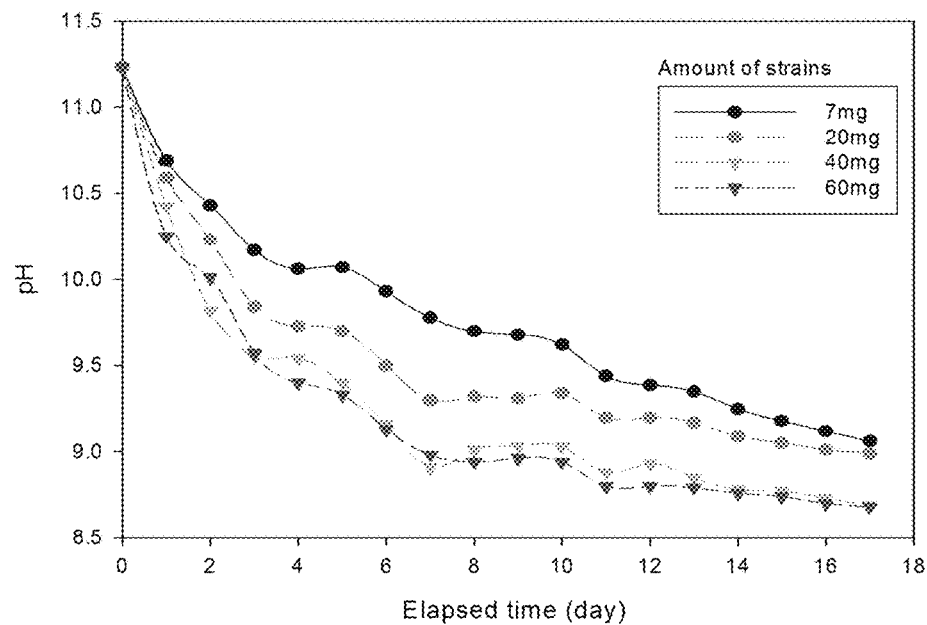
FIGS. 8A and 8B each show (a) pH change and (b) K/S change depending on elapsed days when reducing natural indigo by *Nesterenkonia* sp. KDB4.
Figure 8B:
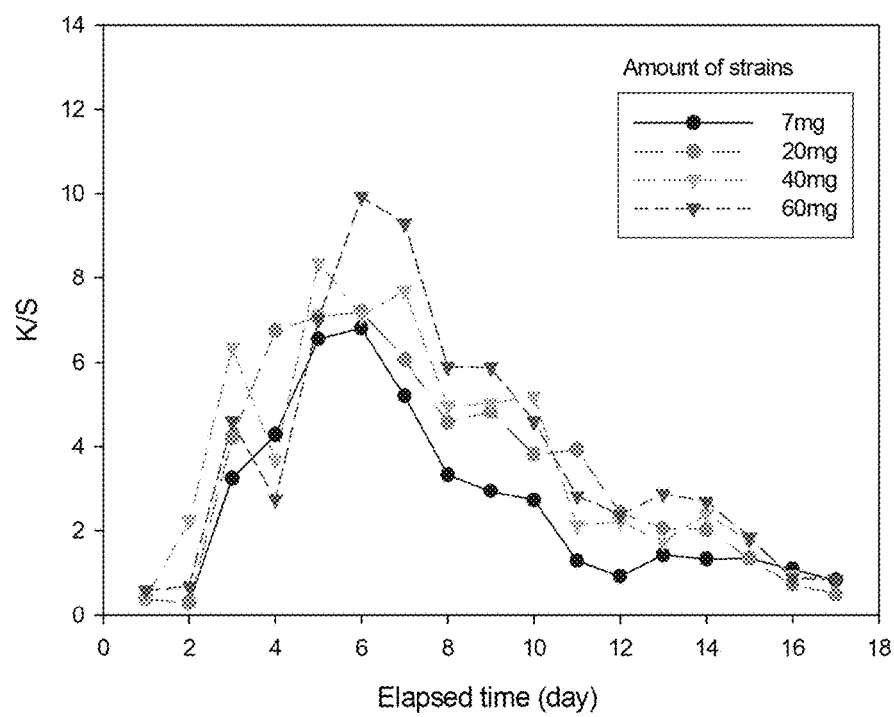

The pH of the reducing solution and change in dye uptake depending on reduction elapsed time when reducing natural indigo by using the bacterial strain *Nesterenkonia* sp. KDB4 were shown in FIG. 8. The pH was continuously reduced as time elapsed up to 40 mg of strain amount, and as the strain amount was increased, the degree of pH reduction depending on the elapsed time was increased, such that the pH value was lower at the same elapsed time. Meanwhile, the pH change in 60 mg of strain amount was not significantly different from that of 40 mg of strain amount even through the strain amount was increased. In the dye uptake, the K/S value was increased up to the day having maximum dye uptake, and decreased afterward. At the same elapsed day, the large strain amount was not necessarily shown with high K/S value.

The pH of dye bath, K/S values and H V/C values of the dyed fabric on the day reduction is initiated, and the reduction day having the maximum dye uptake when reducing natural indigo depending on strain amounts, were shown in Table 15. When reducing the indigo by adding 7 mg of strain, the reduction dyeing was shown on Day 2, and when reducing the indigo by adding 20 mg, 40 mg, and 60 mg of strains, the reduction dyeing was shown immediately after Day 1. The initial dye uptake according to the strain addition amount was 0.30 to 0.59, and accordingly, significant difference was not shown. All cases had PB-series colors. When adding 7 mg, 20 mg, and 60 mg of strains, the maximum dye uptake was shown on Day 6, and when adding 40 mg of strain, the maximum dye uptake was shown on Day 5. Therefore, in all cases, the maximum dye uptake was shown on Day 4 to 5 after the reduction was initiated.

Respective K/S values were 6.81, 7.19, 8.35, and 9.93, and as the strain addition amount was increased, higher K/S value was shown, wherein the pH of the dye bath was lower as the strain addition amount was increased. All of the dyed fabrics had PB-series colors, and as the strain addition amount was increased, the brightness and saturation values were continuously decreased, such that the fabrics were dyed with darker and turbid color.

TABLE 15

<Natural indigo reduction by *Nesterenkonia* sp. KDB 4>

| Strain amount (mg) | Reduction Initiation | | | | Maximum dye uptake | | | |
|---|---|---|---|---|---|---|---|---|
| | Elapsed days | pH | K/S value | H V/C | Elapsed days | pH | K/S value | H V/C |
| 7 | 2 | 10.43 | 0.30 | 3.2PB 7.8/3.0 | 6 | 9.93 | 6.81 | 3.4PB 4.0/5.4 |
| 20 | 1 | 10.59 | 0.40 | 3.2PB 7.5/2.4 | 6 | 9.50 | 7.19 | 3.4PB 3.9/5.2 |
| 40 | 1 | 10.42 | 0.42 | 3.1PB 7.2/2.6 | 5 | 9.40 | 8.35 | 3.6PB 3.8/5.1 |
| 60 | 1 | 10.25 | 0.59 | 2.9PB 6.9/2.6 | 6 | 9.13 | 9.93 | 3.6PB 3.4/5.1 |

Synthetic Indigo Reduction

Figure 9A:
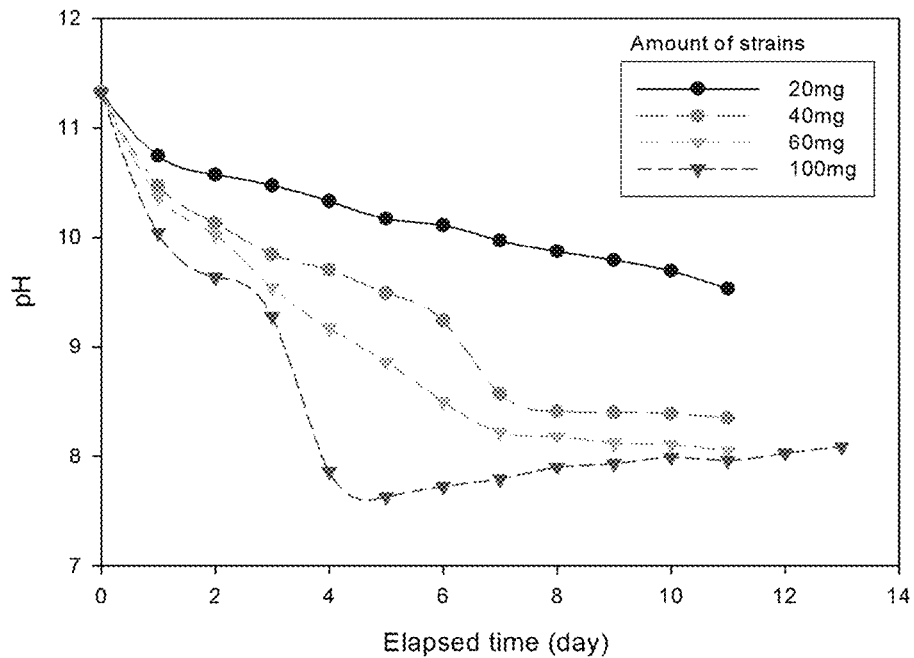
FIGS. 9A and 9B each show (a) pH change and (b) K/S change depending on elapsed days when reducing synthetic indigo by the *Nesterenkonia* sp. KDB4.
Figure 9B:
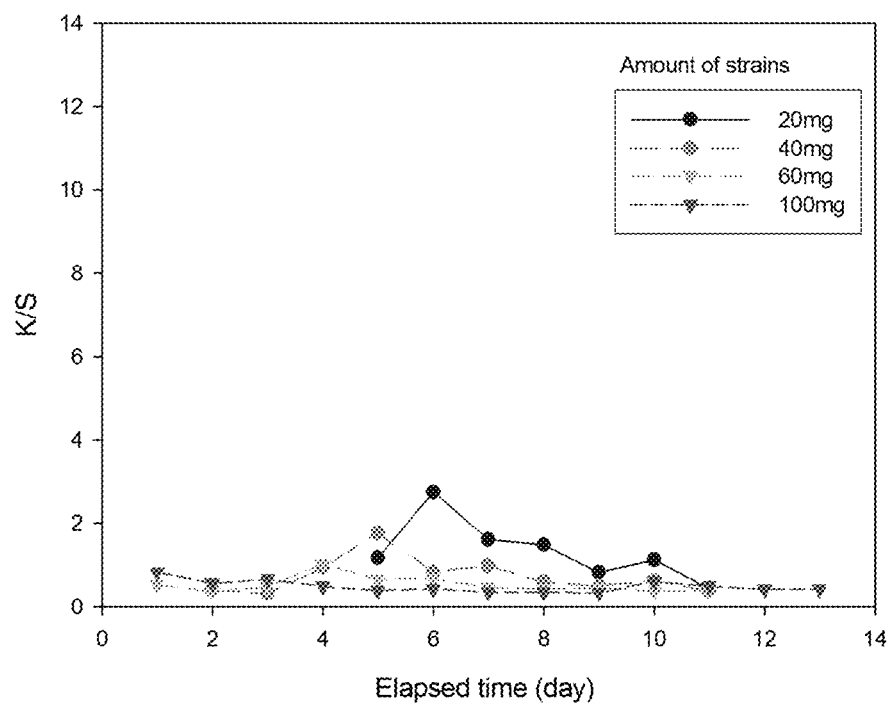

The pH of the reducing solution and change in dye uptake depending on reduction elapsed time up to the reduction end day when reducing synthetic indigo by using the bacterial strain *Nesterenkonia* sp. KDB4 were shown in FIG. 9. The strain amounts were 20 mg, 40 mg, 60 mg, and 100 mg. The pH was continuously reduced as time elapsed in 20 mg of strain amount, and the pH reduction was almost not shown from Day 7 in 40 mg and 60 mg of strain amounts. In 100 mg of strain, the pH was rapidly reduced until Day 4, but after Day 5, pH was rather slightly increased. In 20 mg and 40 mg of strains, the dye uptake was increased until the day having maximum dye uptake, and decreased afterward. However, in 60 mg and 100 mg of strains, significantly low dye uptake were shown in all elapsed days.

The pH of dye bath, K/S values and H V/C values of the dyed fabric on the day reduction is initiated, and the reduction day having the maximum dye uptake of the synthetic indigo depending on the strain amounts, were shown in Table 16. When adding 20 mg of strain, the reduction dyeing was shown on Day 5. When adding 40 mg of strain, the reduction dyeing was shown on Day 2, and when adding 60 mg and 100 mg of strains, the reduction dyeing was shown on Day 1. Respective K/S values were 1.18, 0.41, 0.54, and 0.84, and the maximum dye uptake was shown in 20 mg of strain amount corresponding to the smallest strain amount. 20 mg of strain had the maximum dye uptake on Day (K/S value 2.75), 40 mg of strain had the maximum dye uptake on Day 5 (K/S value 1.77), 60 mg of strain had the maximum dye uptake on Day 4 (K/S value 1.03), and accordingly, as the strain amount was increased, the maximum dye uptake was more rapidly shown by 1 day, whereas the maximum dye uptake was lower as the strain amount was increased. In particular, in 100 mg corresponding to the largest strain amount, the maximum dye uptake (K/S value 0.84) was shown with the reduction initiation, such that the reducing power was the lowest. All cases had PB-series colors, and as the strain addition amount was decreased, the maximum dye uptake was increased, and accordingly, the brightness was low, but the saturation was high. Therefore, all cases were dyed with darker, but clear colors.

TABLE 16

<Synthetic indigo reduction by *Nesterenkonia* sp. KDB 4>

| Strain amount (mg) | Reduction Initiation | | | | Maximum dye uptake | | | |
|---|---|---|---|---|---|---|---|---|
| | Elapsed days | pH | K/S value | H V/C | Elapsed days | pH | K/S value | H V/C |
| 20 | 5 | 10.17 | 1.18 | 3.6PB 6.5/4.4 | 6 | 10.11 | 2.75 | 3.0PB 5.5/5.1 |
| 40 | 2 | 10.13 | 0.41 | 2.7PB 7.5/2.8 | 5 | 9.49 | 1.77 | 3.1PB 6.1/4.7 |
| 60 | 1 | 10.37 | 0.54 | 2.0PB 7.2/3.2 | 4 | 9.17 | 1.03 | 4.0PB 6.4/4.3 |
| 100 | 1 | 10.04 | 0.84 | 2.4PB 6.8/3.6 | 1 | 10.04 | 0.84 | 2.4PB 6.8/3.6 |

Synthetic Indigo Re-reduction

Figure 10A:
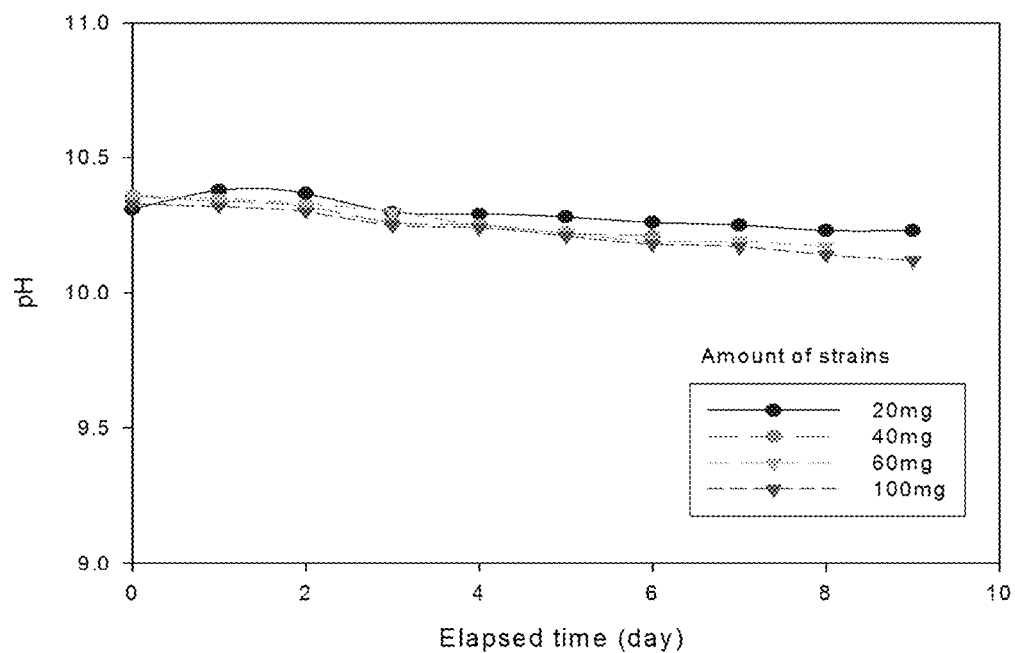
FIGS. 10A and 10B each show (a) pH change and (b) K/S change depending on elapsed days when re-reducing synthetic indigo by the *Nesterenkonia* sp. KDB4.
Figure 10B:
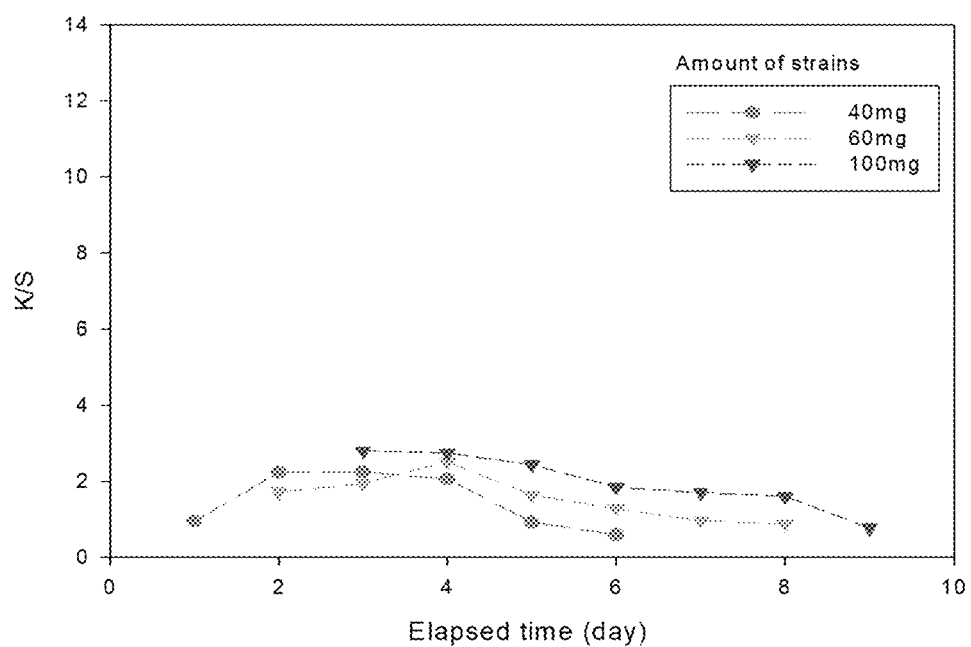
Figure 11:
FIG. 11 shows identification of strain properties through gram-staining.
Figure 12:
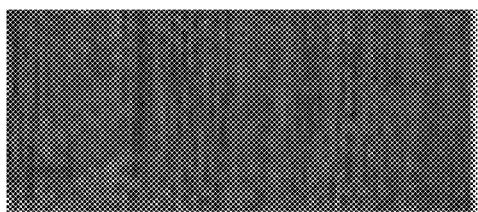
FIG. 12 shows pictures of dyed fabric samples depending on the amounts of strains according to Table 9.
Figure 12:
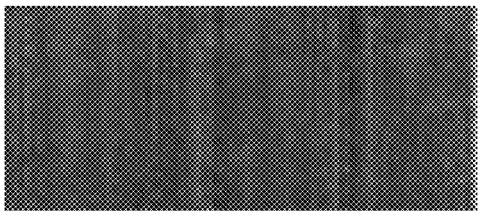
Figure 12:
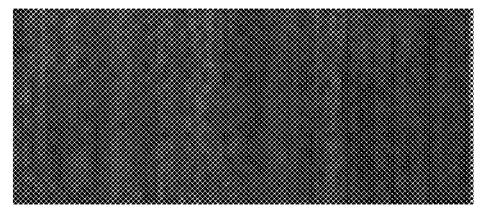
Figure 12:
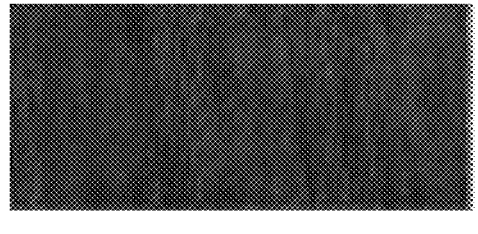
Figure 13:
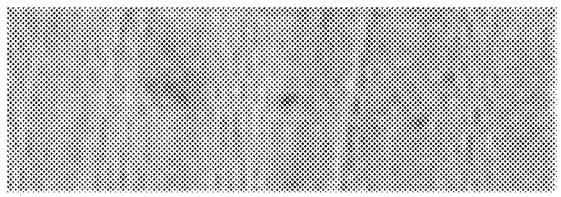
FIG. 13 shows pictures of dyed fabric samples depending on the amounts of strains according to Table 10.
Figure 13:
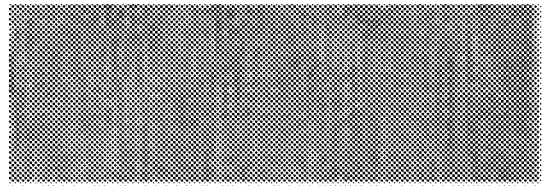
Figure 13:
Figure 14:
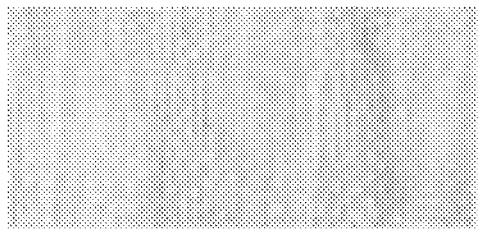
FIG. 14 shows pictures of dyed fabric samples depending on the amounts of strains according to Table 11.
Figure 14:
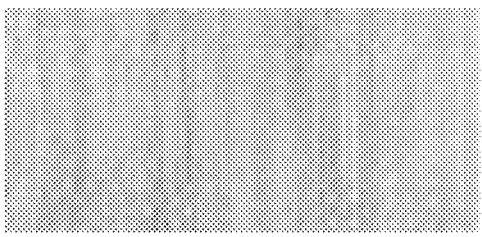
Figure 14:
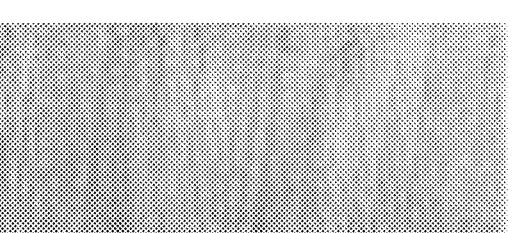
Figure 14:
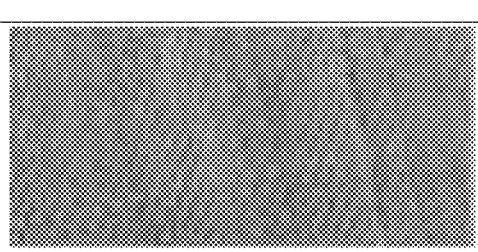
Figure 15:
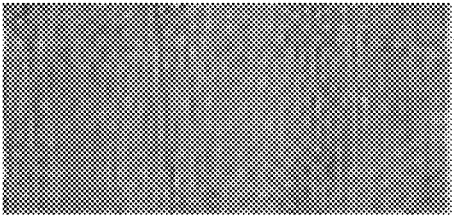
FIG. 15 shows pictures of dyed fabric samples depending on the amounts of strains according to Table 12.
Figure 15:
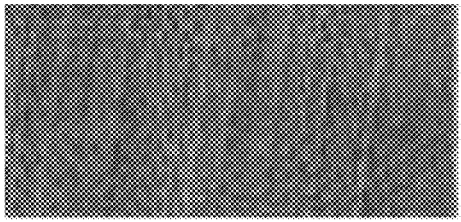
Figure 15:
Figure 15:
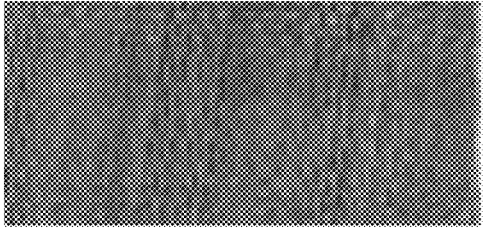
Figure 16:
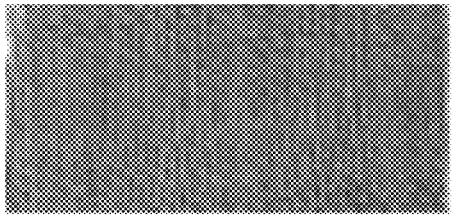
FIG. 16 shows pictures of dyed fabric samples depending on the amounts of strains according to Table 13.
Figure 16:
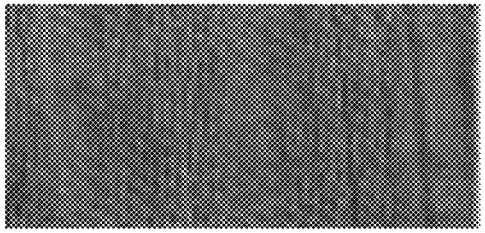
Figure 16:
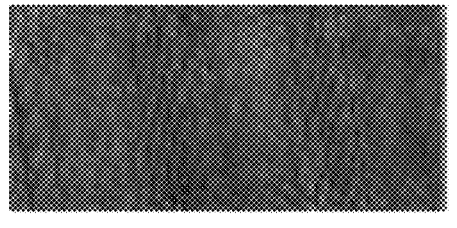
Figure 16:
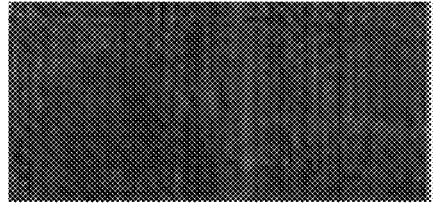
Figure 17:
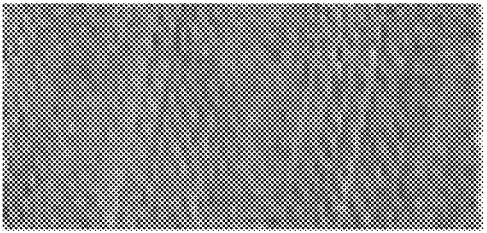
FIG. 17 shows pictures of dyed fabric samples depending on the amounts of strains according to Table 14.
Figure 17:
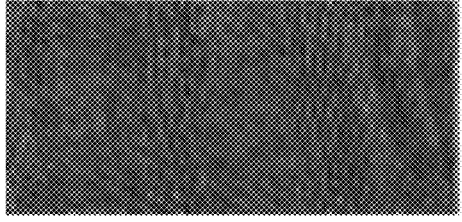
Figure 17:
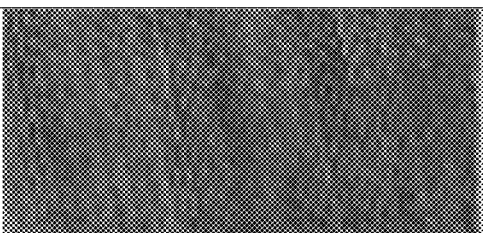
Figure 18:
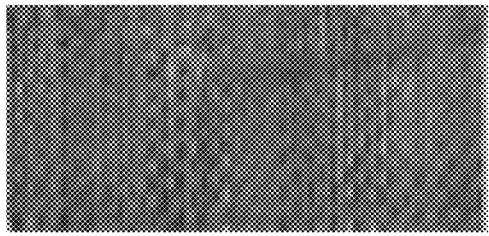
FIG. 18 shows pictures of dyed fabric samples depending on the amounts of strains according to Table 15.
Figure 18:
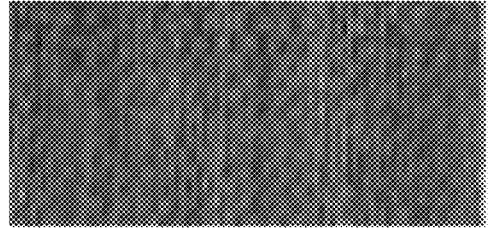
Figure 18:
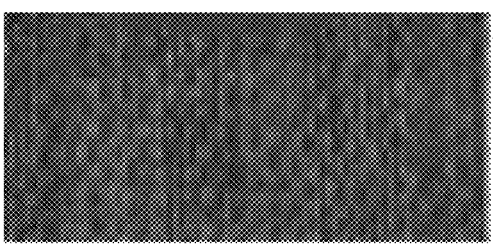
Figure 18:
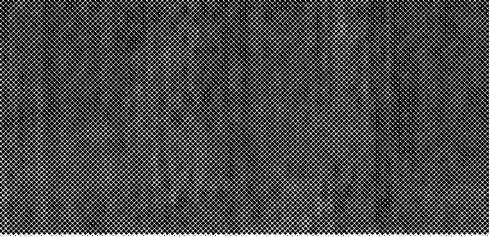
Figure 19:
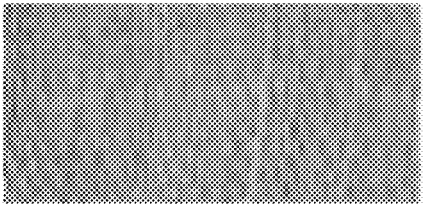
FIG. 19 shows pictures of dyed fabric samples depending on the amounts of strains according to Table 16.
Figure 19:
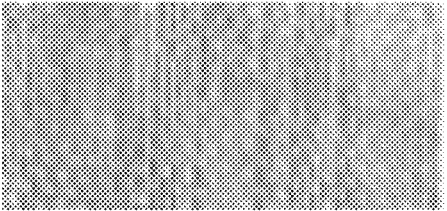
Figure 19:
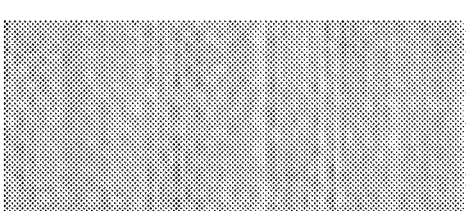
Figure 19:
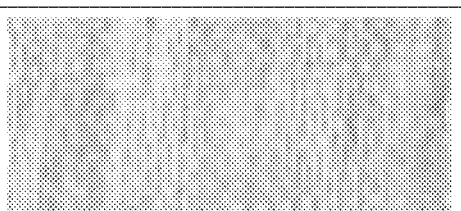
Figure 20:
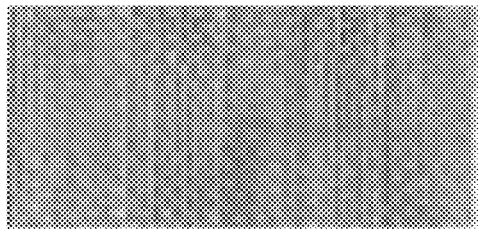
FIG. 20 shows pictures of dyed fabric samples depending on the amounts of strains according to Table 17.
Figure 20:
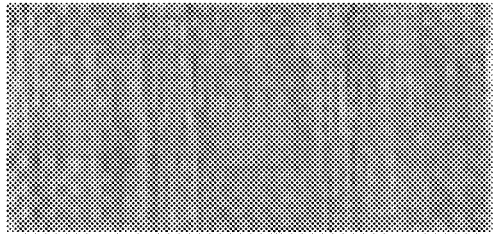
Figure 20:
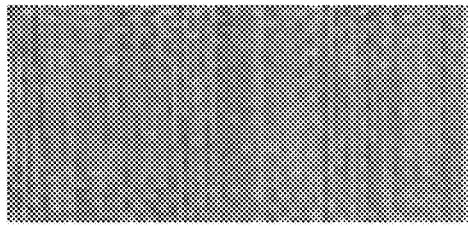

When reducing synthetic indigo by using the bacterial strain *Nesterenkonia* sp. KDB4, after the primary reduction was finished, re-reduction degree was confirmed by adding alkaline to control pH within 10.31 to 10.36. The pH of the reducing solution and change in dye uptake depending on re-reduction elapsed time were shown in FIG. 10. The pH values were 10.12 to 10.23 on Day 9, and regardless of strain amount, the pH reduction was almost not shown as compared to the primary reduction. In 20 mg of strain, the dyeing by re-reduction was not shown. At the same elapsed days, as the strain amount was increased, the dye uptake was slightly high.

The pH of dye bath, K/S values and H V/C values of the dyed fabric on the day re-reduction is initiated, and the day having the maximum dye uptake of the synthetic indigo depending on the strain amounts, were shown in Table 17. In 40 mg of strain, the re-reduction dyeing was shown on the next day after controlling the pH. In 60 mg and 100 mg of strains, the re-reduction dyeing was shown on Day 2 and Day 3, respectively. The dye uptakes of 40 mg, 60 mg, and 100 mg of strains were 0.96, 1.72, and 2.80, respectively, and as the strain amount was increased, the K/S value was higher. 40 mg of strain had the maximum dye uptake on Day (K/S value 2.25), 60 mg of strain had the maximum dye uptake on Day 4 (K/S value 2.52), and 100 mg of strain had the maximum dye uptake on Day 3 (K/S value 2.80), and accordingly, as the strain amount was increased, the K/S value was slightly higher. In 100 mg of strain amount, the dye uptake was continuously decreased after the day reduction is initiated. All cases were dyed with PB-series colors.

TABLE 17

<Synthetic indigo re-reduction by *Nesterenkonia* sp. KDB 3>

| Strain amount (mg) | Reduction initiation | | | | Maximum dye uptake | | | |
|---|---|---|---|---|---|---|---|---|
| | Elapsed days | pH | K/S value | H V/C | Elapsed days | pH | K/S value | H V/C |
| 40 | 1 | 10.34 | 0.96 | 0.8PB 6.5/3.2 | 3 | 10.26 | 2.25 | 3.0PB 5.7/4.8 |
| 60 | 2 | 10.33 | 1.72 | 1.6PB 6.0/4.5 | 4 | 10.25 | 2.52 | 2.5PB 5.4/5.1 |
| 100 | 3 | 10.25 | 2.80 | 3.1PB 5.3/4.8 | 3 | 10.25 | 2.80 | 3.1PB 5.3/4.8 |

The invention claimed is:

1. A reduction dyeing method comprising:
adding to an aqueous solution containing an indigo dye an agent comprising a *Nesterenkonia* sp. KDB4 strain deposited under accession number KCTC 12527BP; and
immersing a fabric in the aqueous solution.

2. The reduction dyeing method of claim 1, wherein the aqueous solution is an alkaline aqueous solution.

3. The reduction dyeing method of claim 1, wherein the strain is a gram-positive bacterium having an activity to assimilate a nitrogen source.

4. The reduction dyeing method of claim 1, wherein the indigo dye is a natural indigo dye or synthetic indigo dye.

5. The reduction dyeing method of claim 1, wherein the strain is an isolated pure strain.

6. The reduction dyeing method of claim 1, the agent is in a form selected from the group consisting of a solution, a powder, a suspension, an aqueous dispersion, an emulsion, an oil dispersion, a paste, a dust, a diffusion material, and granule.

7. The reduction dyeing method of claim 1, wherein the agent further comprises *Nesterenkonia* sp. KDB2 strain deposited under accession number KCTC 12525BP, *Nesterenkonia* sp. KDB3 strain deposited under accession number KCTC 12526B, or a combination thereof.

* * * * *